US011857221B2

(12) United States Patent
Nguyen et al.

(10) Patent No.: US 11,857,221 B2
(45) Date of Patent: Jan. 2, 2024

(54) NESTING TETHER CLAMPING ASSEMBLIES AND RELATED METHODS AND APPARATUS

(71) Applicant: Ortho Development Corporation, Draper, UT (US)

(72) Inventors: Bao-Khang Ngoc Nguyen, Salt Lake City, UT (US); Michael D. Ensign, Salt Lake City, UT (US)

(73) Assignee: Ortho Development Corporation, Draper, UT (US)

( * ) Notice: Subject to any disclaimer, the term of this patent is extended or adjusted under 35 U.S.C. 154(b) by 99 days.

(21) Appl. No.: 17/385,847

(22) Filed: Jul. 26, 2021

(65) Prior Publication Data
US 2021/0353334 A1 Nov. 18, 2021

Related U.S. Application Data

(63) Continuation of application No. 16/276,618, filed on Feb. 15, 2019, now Pat. No. 11,071,569, which is a
(Continued)

(51) Int. Cl.
A61B 17/70 (2006.01)
A61B 17/86 (2006.01)
(Continued)

(52) U.S. Cl.
CPC ........ A61B 17/7022 (2013.01); A61B 17/707 (2013.01); A61B 17/7053 (2013.01);
(Continued)

(58) Field of Classification Search
CPC . A61B 17/70; A61B 17/7022; A61B 17/7047; A61B 17/7049–7058; A61B 17/8869
See application file for complete search history.

(56) References Cited

U.S. PATENT DOCUMENTS 4,156,574 A * 5/1979 Boden ................... F16G 11/101
403/374.2
4,732,180 A 3/1988 Fixel
(Continued)

FOREIGN PATENT DOCUMENTS

AU 2014203469 A1 7/2014
AU 2014201336 A1 10/2014
(Continued)

OTHER PUBLICATIONS

Aug. 26, 2022 Extended European Search Report (12 pgs).
(Continued)

Primary Examiner — Eduardo C Robert
Assistant Examiner — Steven J Cotroneo
(74) Attorney, Agent, or Firm — Matthew D. Thayne; Thayne and Davis LLC

(57) ABSTRACT

Methods for clamping a tether about a spinal or other anatomical feature. In some implementations, a tether may be extended in a loop around an anatomical feature of a spine. A spinal fixation rod may be coupled with an inner coupling piece of a clamping assembly, such as by way of a slot formed in the inner coupling piece. The inner coupling piece may be nestably coupled within an outer coupling piece of the clamping assembly. A first end of the tether may be passed through a passage of the clamping assembly, the passage being is at least partially defined by an outer surface of the inner coupling piece and an inner surface of the outer coupling piece. The loop may be tightened about the anatomical feature with the tether clamped between the inner coupling piece and the outer coupling piece.

20 Claims, 25 Drawing Sheets

Related U.S. Application Data continuation-in-part of application No. 15/674,340, filed on Aug. 10, 2017, now Pat. No. 11,051,857.

(51) Int. Cl.
*A61B 17/88* (2006.01)
*A61B 90/00* (2016.01)
*A61B 17/84* (2006.01)

(52) U.S. Cl.
CPC ...... *A61B 17/8605* (2013.01); *A61B 17/8869* (2013.01); *A61B 17/7032* (2013.01); *A61B 17/7049* (2013.01); *A61B 17/842* (2013.01); *A61B 2090/037* (2016.02)

(56) References Cited

U.S. PATENT DOCUMENTS

| | | |
|---|---|---|
| 5,304,178 A | 4/1994 | Stahurski |
| 5,383,905 A | 1/1995 | Golds et al. |
| 5,413,576 A | 5/1995 | Rivard |
| 5,435,044 A * | 7/1995 | Ida ............ F16G 11/14 24/136 L |
| 5,582,612 A | 12/1996 | Lin |
| 5,702,399 A | 12/1997 | Kilpela et al. |
| 5,938,663 A | 8/1999 | Petreto |
| 6,086,590 A | 7/2000 | Margulies et al. |
| 6,391,030 B1 | 5/2002 | Wagner et al. |
| 6,514,255 B1 | 2/2003 | Ferree |
| 6,656,185 B2 | 12/2003 | Gleason et al. |
| 6,761,720 B1 * | 7/2004 | Senegas ............ A61B 17/7062 606/249 |
| 7,207,090 B2 | 4/2007 | Mattchen |
| 7,481,828 B2 | 1/2009 | Mazda et al. |
| 7,828,830 B2 | 11/2010 | Thramann et al. |
| 7,909,853 B2 * | 3/2011 | Zucherman ........ A61B 17/7065 606/249 |
| 7,959,654 B2 | 6/2011 | Mazda et al. |
| 8,172,843 B2 | 5/2012 | Baccelli et al. |
| 8,221,464 B2 | 7/2012 | Belliard et al. |
| 8,323,318 B2 | 12/2012 | Beccelli et al. |
| 8,323,319 B2 | 12/2012 | Mazda et al. |
| 8,353,962 B2 | 1/2013 | Eckman |
| 8,430,918 B2 | 4/2013 | Baccelli et al. |
| 8,469,967 B2 | 6/2013 | Pratt et al. |
| 8,496,660 B2 | 7/2013 | Carl et al. |
| 8,636,770 B2 | 1/2014 | Hestad et al. |
| 8,721,689 B2 | 5/2014 | Butler et al. |
| 8,728,083 B2 | 5/2014 | Baccelli et al. |
| 8,740,949 B2 * | 6/2014 | Blain ............ A61B 17/82 606/279 |
| 8,747,405 B2 | 6/2014 | Belliard |
| 8,801,759 B2 | 8/2014 | Mazda et al. |
| 8,814,910 B2 | 8/2014 | Baccelli et al. |
| 8,828,055 B2 | 9/2014 | Blain et al. |
| 8,870,870 B2 | 10/2014 | Baccelli et al. |
| 8,906,068 B1 | 12/2014 | Bedor |
| 8,945,188 B2 | 2/2015 | Rezach et al. |
| 8,961,572 B2 | 2/2015 | Kim et al. |
| 8,968,319 B2 | 3/2015 | Chin et al. |
| 8,979,908 B2 | 3/2015 | Lee et al. |
| 9,039,708 B2 | 5/2015 | Larroque-Lahitette |
| 9,078,644 B2 | 7/2015 | Stone |
| 9,101,406 B2 | 8/2015 | Belliard |
| 9,101,425 B2 | 8/2015 | Douget et al. |
| 9,107,720 B2 | 8/2015 | Pratt et al. |
| 9,113,966 B2 | 8/2015 | Baccelli et al. |
| 9,119,675 B2 | 9/2015 | Lee et al. |
| 9,144,440 B2 | 9/2015 | Aminian |
| 9,186,185 B2 | 11/2015 | Hestad et al. |
| 9,192,367 B2 | 11/2015 | Nunley et al. |
| 9,295,496 B2 | 3/2016 | Le Couedic et al. |
| 9,345,518 B2 * | 5/2016 | Larroque-Lahitette ............ A61B 17/7053 |
| 9,393,051 B2 | 7/2016 | Baccelli et al. |
| 9,402,666 B2 | 8/2016 | Al Shail et al. |
| 9,433,441 B2 | 9/2016 | George et al. |
| 9,579,127 B2 | 2/2017 | Kostuik et al. |
| 9,585,705 B2 | 3/2017 | Koch et al. |
| 2002/0116013 A1 * | 8/2002 | Gleason ............ A61F 2/08 606/151 |
| 2004/0243131 A1 | 12/2004 | Dirks et al. |
| 2006/0271055 A1 | 11/2006 | Thramann |
| 2007/0191844 A1 | 8/2007 | Carls et al. |
| 2009/0248077 A1 | 10/2009 | Johns |
| 2011/0112581 A1 * | 5/2011 | Clement ............ A61B 17/7053 606/264 |
| 2011/0238188 A1 | 9/2011 | Baccelli et al. |
| 2011/0245875 A1 | 10/2011 | Karim |
| 2011/0288589 A1 | 11/2011 | Fielding et al. |
| 2012/0022592 A1 * | 1/2012 | Belliard ............ A61B 17/7053 606/279 |
| 2012/0130373 A1 | 5/2012 | Larroque-Lahitette |
| 2012/0271354 A1 * | 10/2012 | Baccelli ............ A61B 17/7053 606/279 |
| 2012/0303065 A1 | 11/2012 | Larroque-Lahitette et al. |
| 2012/0303121 A1 * | 11/2012 | Douget ............ A61B 17/84 623/13.14 |
| 2012/0323280 A1 | 12/2012 | Chin et al. |
| 2013/0237990 A1 | 9/2013 | Nunley et al. |
| 2013/0261625 A1 | 10/2013 | Koch et al. |
| 2013/0261668 A1 | 10/2013 | Douget et al. |
| 2014/0074172 A1 | 3/2014 | Lee et al. |
| 2014/0094850 A1 | 4/2014 | Clement et al. |
| 2014/0114356 A1 | 4/2014 | Le Couedic et al. |
| 2014/0148854 A1 | 5/2014 | Carlson et al. |
| 2014/0214040 A1 | 7/2014 | Carl et al. |
| 2014/0257397 A1 | 9/2014 | Akbarnia et al. |
| 2014/0257401 A1 * | 9/2014 | George ............ A61B 17/7041 606/278 |
| 2014/0277162 A1 | 9/2014 | Kostuik et al. |
| 2014/0336708 A1 | 11/2014 | Mazda et al. |
| 2015/0112389 A1 | 4/2015 | Le Couedic et al. |
| 2015/0119938 A1 | 4/2015 | Lee et al. |
| 2015/0164561 A1 * | 6/2015 | Simpson ............ A61B 17/7086 606/279 |
| 2015/0223845 A1 * | 8/2015 | Larroque-Lahitette ............ A61B 17/7032 606/265 |
| 2015/0305782 A1 | 10/2015 | Baccelli et al. |
| 2015/0320448 A1 | 11/2015 | Legallois |
| 2015/0366598 A1 | 12/2015 | Douget et al. |
| 2016/0106478 A1 | 4/2016 | Simpson et al. |
| 2016/0157896 A1 * | 6/2016 | Palmer ............ A61B 17/7053 606/278 |
| 2016/0213404 A1 | 7/2016 | Al Shail et al. |
| 2016/0249957 A1 * | 9/2016 | Deneuvillers ...... A61B 17/7053 606/263 |
| 2017/0086888 A1 | 3/2017 | Simpson et al. |
| 2017/0172631 A1 * | 6/2017 | Mosnier ............ A61B 17/7043 |
| 2017/0189076 A1 | 7/2017 | Belliard |
| 2017/0360484 A1 * | 12/2017 | Pasquet ............ A61B 17/82 |
| 2018/0132906 A1 * | 5/2018 | Simpson ............ A61B 17/7053 |
| 2019/0046244 A1 | 2/2019 | Nguyen et al. |

FOREIGN PATENT DOCUMENTS

| | | |
|---|---|---|
| AU | 2014201339 A1 | 10/2014 |
| EP | 597258 A1 | 5/1994 |
| EP | 2465457 A1 | 6/2012 |
| EP | 2465456 B1 | 6/2013 |
| EP | 2716262 A1 | 4/2014 |
| EP | 2730242 | 5/2014 |
| EP | 2725993 | 3/2015 |
| EP | 2716262 B1 | 5/2015 |
| WO | 2002/09604 | 2/2002 |
| WO | 2006119447 | 11/2006 |
| WO | 2013001180 | 1/2013 |
| WO | 2016/116692 | 7/2016 |

(56) References Cited

OTHER PUBLICATIONS

EP2725993B1—Machine translation.
EP2716262B1—Machine translation.
EP2716262A1—Machine translation.
Panjabi, et al., Biomechanical Evaluation of Spinal Fixation Devices: II. Stability Provided by Eight Internal Fixation Devices, Spine, vol. 13, No. 10, pp. 1135-1140, May 15, 1988.
Apr. 2, 2019, PCT/US2019/015698 International Search Report (2 pgs).
Apr. 2, 2019, PCT/US2019/015698 Written Opinion (5 pgs).
U.S. Appl. No. 15/674,340, Non-Final Office Action dated Dec. 12, 2018 (11 pgs).
May 7, 2020, PCT/US20/18415 International Search Report (2 pgs).
May 7, 2020, PCT/US20/18415 Written Opinion (8 pgs).
U.S. Appl. No. 16/276,618, Non-Final Office Action dated Jul. 21, 2020 (9 pgs).
U.S. Appl. No. 15/674,340, Non-Final Office Action dated Jul. 11, 2019 (12 pgs).
U.S. Appl. No. 15/674,340, Final Office Action dated Jan. 31, 2020 (10 pgs).
U.S. Appl. No. 15/674,340, Non-Final Office Action dated Oct. 9, 2020 (9 pgs).

* cited by examiner

NESTING TETHER CLAMPING ASSEMBLIES AND RELATED METHODS AND APPARATUS

RELATED APPLICATIONS

This is a continuation of co-pending U.S. patent application Ser. No. 16/276,618 filed Feb. 15, 2019 and titled "TETHER CLAMPING ASSEMBLIES AND RELATED METHODS AND APPARATUS," which is continuation-in-part of U.S. patent application Ser. No. 15/674,340 filed Aug. 10, 2017 and also titled "TETHER CLAMPING ASSEMBLIES AND RELATED METHODS AND APPARATUS," both applications of which are hereby incorporated herein by reference in their entireties.

SUMMARY

Disclosed herein are various embodiments of tether clamping assemblies, along with related bone fixation assemblies with which the tether clamping assemblies may be used, along with various other inventive methods and devices. In preferred embodiments, the tether clamping assemblies may be configured to both receive and lock one or more tether portions therein and also to be coupled with a fixation member, such as an elongated rod. Thus, the inventive devices, features, and methods disclosed herein may be particularly suitable for use in connection with spinal fixation. However, it is contemplated that the inventive features, and methods disclosed herein may also be used in other medical implants and/or devices, as disclosed in greater detail below.

In a more particular example of a spinal fixation assembly according to some embodiments, the assembly may comprise a tether configured to engage a spinal feature of a patient's spine, such as a spinous process, transverse process, and/or spinal lamina. In some embodiments, the tether may be devoid of locking teeth. Thus, in some such embodiments, the tether may be smooth, or at least substantially smooth. In some embodiments, the tether may comprise a flattened tether having a rectangular cross-sectional shape. In some embodiments, the tether may comprise opposing surfaces that are at least substantially uniform in roughness. In some such embodiments, both opposing surfaces may be smooth, or at least substantially smooth.

The spinal fixation assembly may further comprise a tether clamping assembly, which may comprise a first coupling piece and a second coupling piece configured to be coupled with the first coupling piece. In some such embodiments, the first coupling piece may comprise an inner coupling piece, the second coupling piece may comprise an outer coupling piece, and the inner coupling piece may be configured to be nested or otherwise received within the outer coupling piece.

The tether clamping assembly may comprise a first passage configured to receive a first portion of the tether and, in some embodiments, a second passage configured to receive a second portion of the tether. One or both passages may be configured to provide for a wedge lock of the tether therein. This may be provided, for example, by providing opposing surfaces defining the passage(s), which surfaces may be part of inner and outer surfaces of an outer and inner coupling piece of the assembly, respectively, that are tapered in the same direction relative to a central axis of the tether clamping assembly, which may coincide with the axis of a cap and/or set screw in some embodiments. In some embodiments, the respective angles of the two surfaces may differ slightly to enhance this wedge lock. Alternatively, however, the two surfaces may taper at the same, or at least substantially the same, angle.

In some embodiments, the first passage may be defined by a first surface and a second surface, wherein the first surface comprises a surface roughness greater than a surface roughness of the second surface, and wherein the first passage is configured such that the tether can be clamped in between the first surface and the second surface so as to allow the tether to move through the first passage in a first direction and lock the tether in place so as to at least substantially prevent the tether from moving through the first passage in a second direction opposite from the first direction.

Some embodiments may further comprise a second passage configured to receive a second portion of the tether to define a tether loop for engaging the spinal feature. In some such embodiments, the second passage may also be defined by a first surface and a second surface, wherein the first surface of the second passage comprises a surface roughness greater than a surface roughness of the second surface of the second passage.

In some embodiments, the first surface of one or both passages may be formed on an inner wall of the outer coupling piece, and the second surface may be formed on an outer wall of the inner coupling piece. To provide a desired surface roughness differential between the two opposing surfaces of one or both of the passages, the first surface may comprise a plurality of projections configured to engage the tether. The plurality of projections may be defined by, for example, a plurality of elongated grooves and/or a plurality of teeth. In some embodiments, the second surface of one or both passages may be smooth.

In another specific example of a tether clamping assembly according to some embodiments, the assembly may comprise a tether configured to engage a bone, such as a portion of a patient's spine. The assembly may further comprise an inner coupling piece and an outer coupling piece configured to receive the inner coupling piece. A first passage may be at least partially defined by an inner surface of the outer coupling piece and an outer surface of the inner coupling piece and configured to receive the tether therethrough. The first passage may be configured such that the tether can be clamped in between the inner surface and the outer surface so as to allow the tether to move through the first passage in a first direction and lock the tether in place so as to at least substantially prevent the tether from moving through the first passage in a second direction opposite from the first direction. In some embodiments, at least one of the inner surface and the outer surface comprises a plurality of projections configured to engage the tether and/or may be contoured and/or surface roughened to provide a frictional differential.

In some embodiments, only one of the inner surface and the outer surface comprises a plurality of projections configured to engage the tether.

Some embodiments may further comprise a second passage at least partially defined by an inner surface of the outer coupling piece and an outer surface of the inner coupling piece. The second passage may be configured to receive a second portion of the tether therethrough so as to define a tether loop for engaging the bone. Similar to the first passage, in some embodiments, the second passage may be configured such that the tether can be clamped in between the inner surface of the second passage and the outer surface of the second passage so as to allow the tether to move through the second passage in a first direction and lock the tether in place so as to at least substantially prevent the tether from moving through the second passage in a second direction opposite from the first direction.

Some embodiments may further comprise a cap. In some such embodiments, the cap may be configured to engage the inner coupling piece, such as by threadably engaging the inner coupling piece. In some embodiments in which the cap is threaded, the cap may be configured to engage a threaded opening formed on the inner coupling piece. The cap may also, or alternatively comprise a flange, which may be configured to engage the outer coupling piece.

In a specific example of method for fixation of a tether to an anatomical feature, the method may comprise extending a flexible tether in a loop around an anatomical feature of a patient, such as a spinal feature. An elongate member, such as a rod, may be coupled with a clamping assembly. A first end of the flexible tether may be extended or otherwise positioned through a first passage of the clamping assembly. The first passage may be defined by a first pair of opposing surfaces, preferably having distinct surface roughnesses. In some implementations, a second end of the flexible tether opposite from the first end may be extended or otherwise positioned through a second passage defined by a second pair of opposing surfaces also preferably having distinct surface roughnesses. In some implementations, the steps of positioning the first end of the flexible tether through the first passage and positioning the second end of the flexible tether through the second passage lock the flexible tether in place about the anatomical feature without use of a secondary locking feature and/or step, and/or without the use of any tensioning instrumentation to prevent the size of the loop from increasing.

In some implementations, the clamping assembly may comprise an inner coupling piece and an outer coupling piece configured to receive the inner coupling piece. In some such implementations, one or both of the first passage and the second passage may be at least partially defined by an inner surface of the outer coupling piece and an outer surface of the inner coupling piece.

In some implementations in which the elongate member comprises a rod, the inner coupling piece may comprise a slot configured to receive and engage the rod. Thus, in some such implementations, the step of coupling the elongate member with the clamping assembly may comprise engaging the rod with the slot.

In still another specific example of a spinal fixation assembly according to some embodiments, the assembly may comprise a first coupling piece, which may comprise an inner coupling piece, and a second coupling piece, which may comprise an outer coupling piece, configured to be nestably coupled with the first/inner coupling piece. The assembly may define a first passage configured to receive a first portion of a tether. The first passage may be defined at least in part (in some such embodiments, wholly) by a first external surface of the first coupling piece and first internal surface of the second coupling piece. The assembly may further define a second passage configured to receive a second portion of the tether so as to define a loop for engaging a spinal feature of a patient. The second passage may be defined at least in part (in some such embodiments, wholly) by a second external surface of the first coupling piece and a second internal surface of the second coupling piece. The first and second passages may be configured such that the tether can be clamped in between the first coupling piece and the second coupling piece so as to provide a force differential between extending the tether through the first and second passages in a first direction and in a second direction at least substantially opposite the first direction to facilitate tightening the loop around the spinal feature while inhibiting loosening of the tether around the spinal feature.

In some embodiments, the first passage and the second passage may each be further defined by a pair of opposing apertures formed within the first coupling piece. In some such embodiments, the first and second passages may be positioned in respective legs extending from a body portion of the first and/or inner coupling piece.

In some embodiments, the first coupling piece may further comprise a slot configured to receive an elongate member therethrough, such as a cylindrical rod. The slot may be formed in the body portion of the first/inner coupling piece. In some embodiments, the slot may comprise a shape configured to prevent the cylindrical rod from being removed from the slot in a direction transverse to an axis of the cylindrical rod without deforming the slot.

In some embodiments, the first coupling piece may further comprise a shaft, which may be threaded. In some such embodiments, the spinal fixation assembly may further comprise a cap configured to threadably engage the threaded shaft. The cap may therefore, for example, comprise a female threaded opening. In some embodiments, the spinal fixation assembly may be configured such that threading the cap onto the threaded shaft draws the first coupling piece towards the second coupling piece. The cap may be configured to pinch opposing portions of the tether between the cap and the second coupling piece.

In some embodiments, the first surface and the second surface may taper so as to create a wedge lock for clamping the tether therebetween. For example, the first surface and the second surface may taper relative to a central axis of the assembly and/or a central axis of the first coupling piece.

In another example of a tether clamping assembly according to some embodiments, the assembly may comprise an inner coupling piece comprising a slot configured to receive a rod therein and a shaft. The assembly may further comprise a pair of opposing outer surfaces, which may be formed on the inner coupling piece, and may further comprise an outer coupling piece configured to nestably receive the inner coupling piece. The outer coupling piece may comprise a pair of opposing inner surfaces configured to be positioned adjacent to the pair of opposing outer surfaces of the inner coupling piece so as to at least partially define a pair of opposing passages configured to receive a tether therethrough and clamp the tether between the inner coupling piece and the outer coupling piece.

Some embodiments may further comprise a cap configured to fixedly engage the shaft. The cap may comprise a threaded opening configured to threadably receive a shaft formed on the inner coupling piece. In some such embodiments, the tether clamping assembly may be configured such that threading the cap onto the threaded shaft draws the inner coupling piece towards the outer coupling piece. In some embodiments, the tether clamping assembly may be further configured such that threading the cap onto the threaded shaft pinches the tether between the cap and the inner coupling piece to secure the tether in a loop about an anatomical feature of a patient.

In some embodiments, the pair of opposing passages may taper together so as to create a wedge lock for clamping the tether therebetween. For example, the inner and outer surfaces defining the passages may taper relative to an axis of the shaft or another element of the assembly. In some embodiments, the shaft may terminate at a first end of the inner coupling piece, and the pair of opposing passages may taper towards one another in a direction towards the first end.

In some embodiments, the inner coupling piece may further comprise a pair of opposing apertures. In some such embodiments, each of the pair of opposing passages may be further defined by a respective aperture of the pair of opposing apertures.

In an example of a method for fixation of a tether to an anatomical feature, such as a spinal feature, according to some implementations, the method may comprise extending a flexible tether in a loop around a spinal or other anatomical feature of a patient. An elongate member, such as a rod, may be coupled with an inner coupling piece of a clamping assembly. The inner coupling piece may be nested within an outer coupling piece of the clamping assembly and a first end of the flexible tether may be extended through a first passage of the clamping assembly. The clamping assembly may be configured such that the first passage is at least partially defined by an outer surface of the inner coupling piece and an inner surface of the outer coupling piece. A second end of the flexible tether opposite from the first end may be extended through a second passage. The clamping assembly may be configured such that the second passage is at least partially defined by an outer surface of the inner coupling piece and an inner surface of the outer coupling piece. The loop may then be tightened and/or locked about the anatomical feature with the flexible tether clamped between the inner coupling piece and the outer coupling piece. The clamping assembly may be further configured such that the step of tightening the loop requires less force than loosening the loop, preferably without the use of any additional features, components, or steps.

In some implementations, at least a portion of the surfaces defining the first passage are distinct, such as separated, from at least a portion of the surfaces defining the second passage. In some such implementations, the surfaces defining the first passage are wholly distinct from the surfaces defining the second passage.

In some implementations, the step of tightening and/or locking the loop about the anatomical feature with the flexible tether clamped between the inner coupling piece and the outer coupling piece may comprise pulling on one or both loose ends of the flexible tether without use of a secondary locking feature.

Some implementations may further comprise, after the step of tightening the loop about the anatomical feature with the flexible tether clamped between the inner coupling piece and the outer coupling piece, threadably coupling a locking cap with the inner coupling piece to pinch the flexible tether in between the locking cap and the outer coupling piece.

The features, structures, steps, or characteristics disclosed herein in connection with one embodiment may be combined in any suitable manner in one or more alternative embodiments.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

A detailed description of apparatus, systems, and methods consistent with various embodiments of the present disclosure is provided below. While several embodiments are described, it should be understood that the disclosure is not limited to any of the specific embodiments disclosed, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

Apparatus, methods, and systems are disclosed herein relating to spinal fixation or other bone fixation. In some embodiments, tether clamping assemblies may be provided, such as clamping assemblies used to clamp a tether about a spinal feature to assist in spinal fixation. More particularly, in some embodiments, a tether clamping assembly may also be configured to engage a spinal fixation rod. In preferred embodiments, the clamping assembly may be configured such that one or more portions of a tether may be self-locked therein without requiring any additional locking elements, features, or steps. In this manner, for example, a tether may be looped around a spinal feature or other anatomical feature, coupled with a fixation element, such as a rod, and then locked in place to stabilize the anatomical feature.

The embodiments of the disclosure may be best understood by reference to the drawings, wherein like parts may be designated by like numerals. It will be readily understood that the components of the disclosed embodiments, as generally described and illustrated in the figures herein, could be arranged and designed in a wide variety of different configurations. Thus, the following detailed description of the embodiments of the apparatus and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified. Additional details regarding certain preferred embodiments and implementations will now be described in greater detail with reference to the accompanying drawings.

Figure 1:
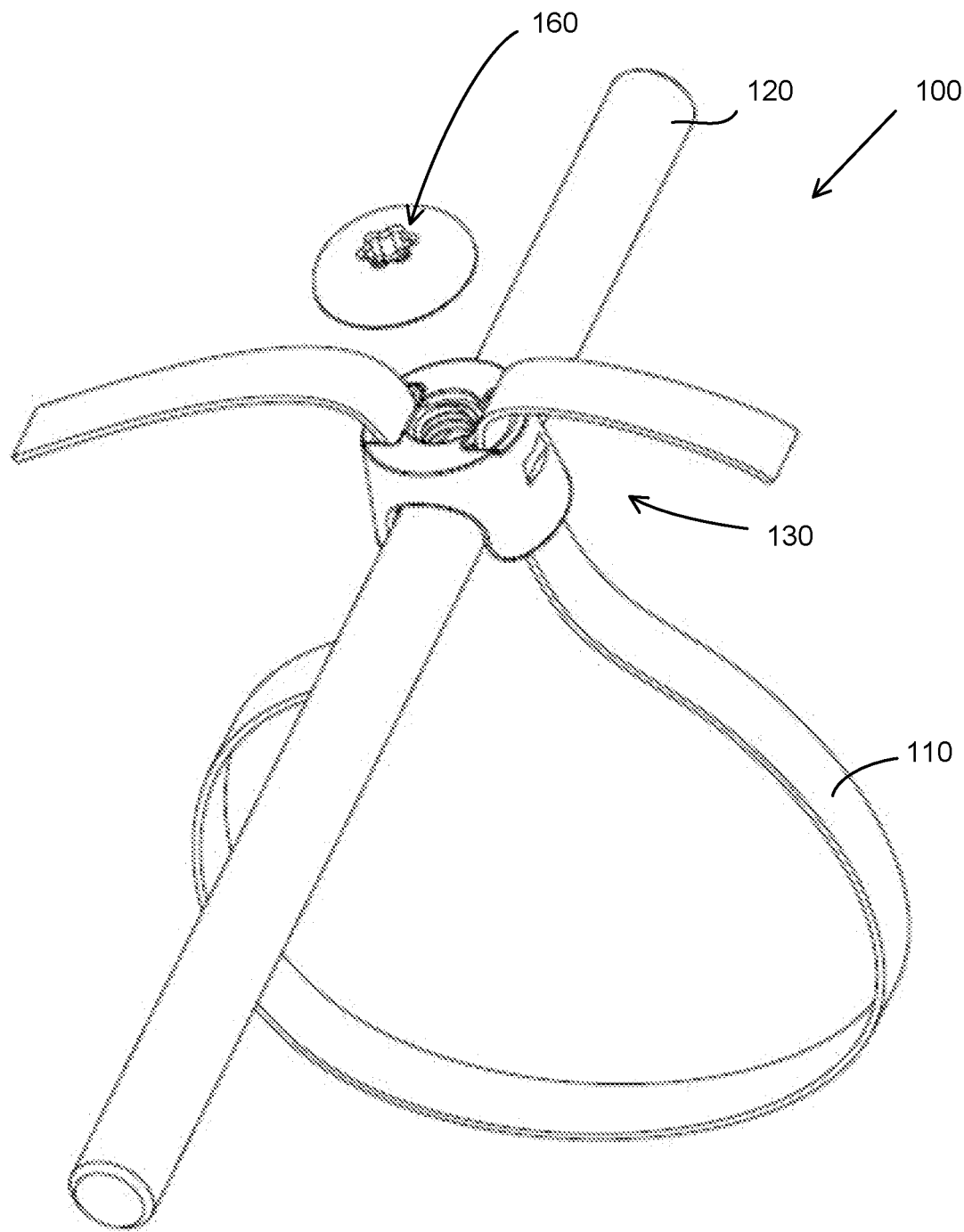
FIG. 1 is an exploded, perspective view of a spinal fixation assembly including a tether clamping assembly according to some embodiments.

FIG. 1 is an exploded view of a spinal fixation assembly 100 according to some embodiments. Assembly 100 comprises a tether 110 that is configured to engage a spinal feature of a patient's spine, such as, in preferred embodiments, looped around the spinal lamina and/or other spinal features, such as the transverse processes of the patient's spine. Tether 110 in some embodiments, may comprise a flat, flexible band resembling, for example, a piece of tape. In preferred embodiments, tether 110 may be flat and/or smooth on both opposing sides. For example, in preferred embodiments tether 110 may be devoid of locking teeth and/or other projections.

Assembly 100 further comprises a tether clamping assembly 130 configured to engage and couple a coupling member, such as a rod 120 or other elongate member, with the tether 110 so as to facilitate coupling of a patient's spine in a desired position without use of pedicle screws or other similar bone-invasive components. Assembly 100 further comprises a cap 160 configured to engage tether clamping assembly 130, as described in greater detail below. Although preferred embodiments disclosed herein, including assembly 100, may be configured to allow for coupling of a tether with spinal features, it is contemplated that the inventive principles disclosed herein may be applied to provide for clamping/securing of a tether to other anatomical features, such as securing two portions of a broken or cracked bone, such as a femur, for example. In some such embodiments not involving spinal anatomy, the spinal rod or other fixation member discussed below may be omitted. In some such embodiments, the bone itself may be clamped by the clamping assembly 130 instead of clamping both the tether and the rod/fixation member.

Figure 2A:
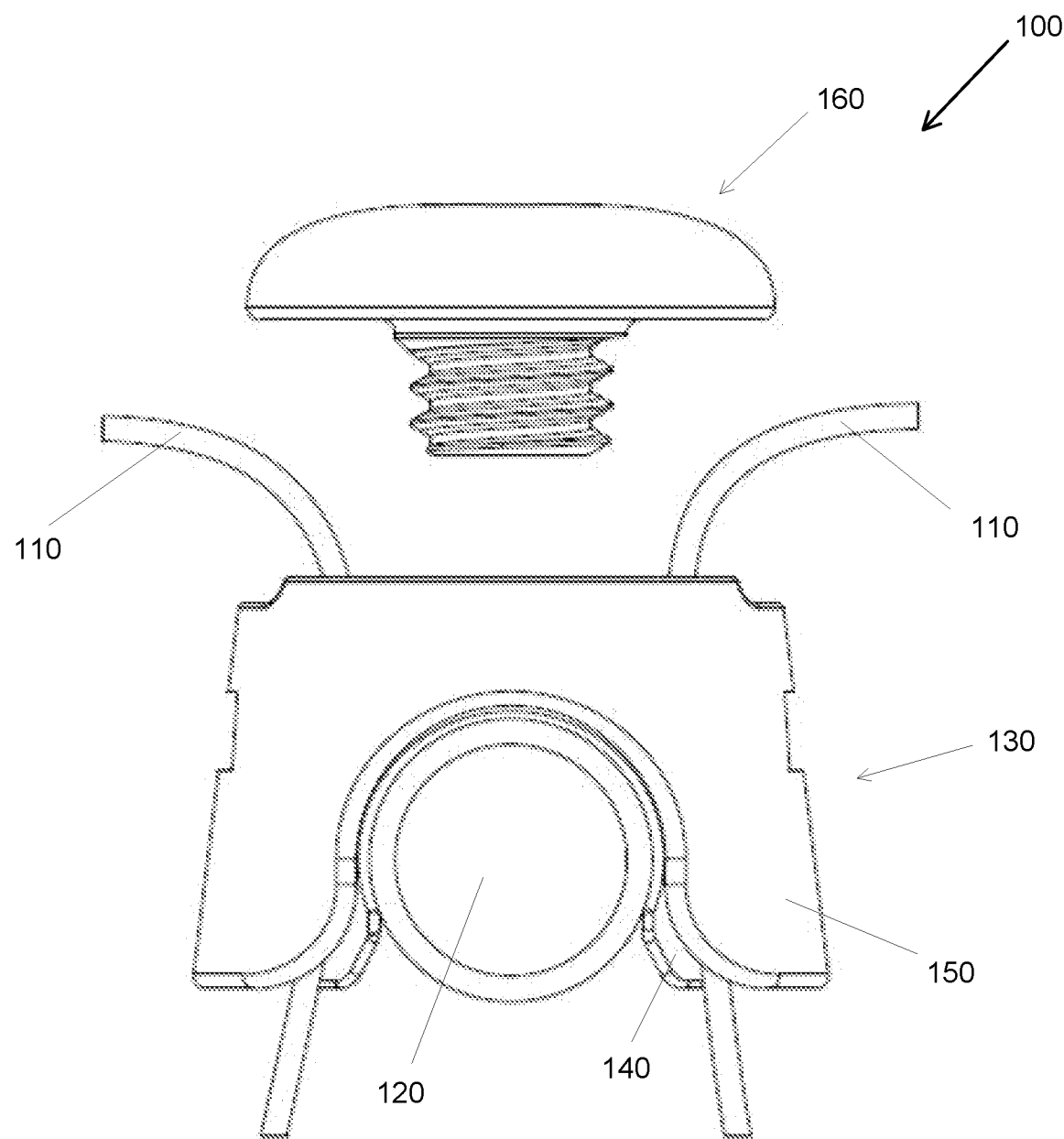
FIG. 2A is an exploded, side elevation view of the spinal fixation assembly of FIG. 1.

FIG. 2A is a side elevation view of spinal fixation assembly 100. As shown in this figure, tether clamping assembly 130 comprises two separate pieces, namely, a first or inner coupling piece 140 and a second or outer coupling piece 150 configured to be coupled with the first coupling piece 140.

First/inner coupling piece 140 defines a slot 145 for receipt of a rod 120 or other elongate and/or rigid coupling member therethrough. Preferably, slot 145 is shaped to match, or at least substantially match, the shape of the outer surface of rod 120 such that rod 120 may be firmed engaged/gripped by slot 145. In some embodiments, slot 145 may comprise a plurality of engagement features 141, such as teeth, grooves, spikes, or a contoured and/or roughened surface to further facilitate a firm engagement between rod 120 and inner coupling piece 140. This roughening may be applied, in some embodiments, by way of diamond plating, blasting, etc. In some embodiments, one or both of the coupling pieces may comprise features that allow for slot 145 to resiliently flex to receive rod 120 therein and then snap back in place to fixedly engage rod 120, as discussed in greater detail below.

In embodiments providing a snap-on feature, slot 145 may also be roughened, textured, and or provided with teeth or other engagement features 141, as mentioned above. In this manner, the inner coupling piece 140 may be snapped onto the rod 120 and the inner coupling piece 140 may be held in place on the rod without requiring a practitioner to hold it in place by virtue of the engagement features 141 and/or a textured or roughened surface. However, in order to allow the inner coupling piece 140 to be slid to its desired location on the rod 120, it may be preferred that the frictional engagement be configured so as to allow a practitioner to manually overcome the friction to move the inner coupling piece 140 and/or assembly 100 as needed during surgery.

Figure 2B:
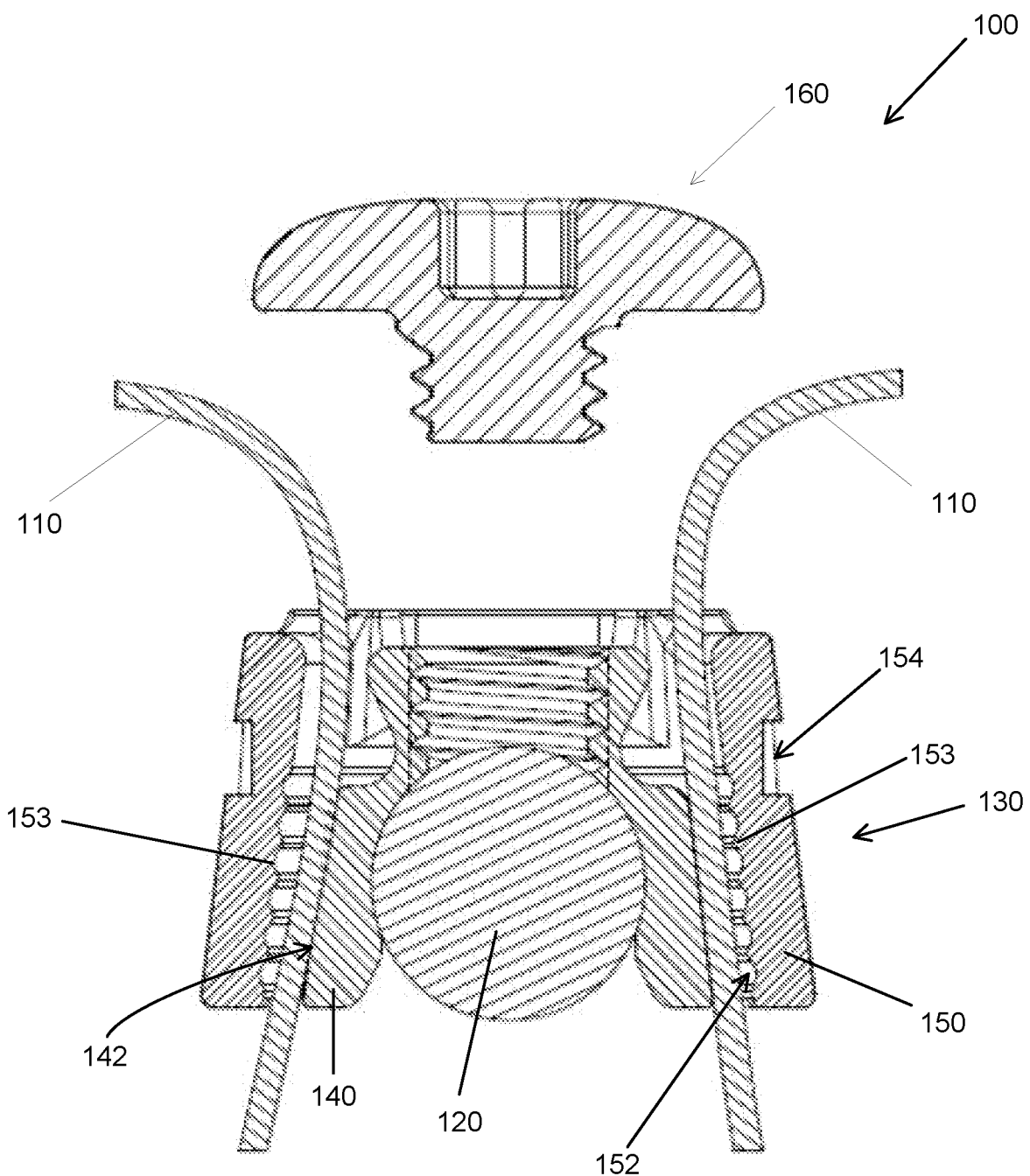
FIG. 2B is a cross-sectional view of the spinal fixation assembly of FIG. 2A.

FIG. 2B is a cross-sectional view of spinal fixation assembly 100. As depicted in this figure, first/inner coupling piece 140 is configured to be received within second/outer coupling piece 150 in a nesting fashion. In some embodiments, including the depicted embodiment, first/inner coupling piece 140 is configured to be wholly received within second/outer coupling piece 150. However, it is contemplated that, in other embodiments, a portion of the outer coupling piece may protrude from the inner coupling piece or, as discussed in connection with another embodiment below, tether clamping assembly 130 may instead comprise a single element.

Second/outer coupling piece 150 may similarly comprise a slot 155 that may be configured to be aligned with slot 145 upon coupling inner coupling piece 140 with outer coupling piece 150. By coupling inner coupling piece 140 with outer coupling piece 150, a pair of opposing passages are defined for receipt of separate portions of tether 110 therethrough.

Thus, first and second passages may be defined, respectively, by an inner surface 152 of outer coupling piece 150 and an outer surface 142 of inner coupling piece 140, both of which may be configured to receive separate portions of tether 110 therethrough. In preferred embodiments, clamping assembly 130 is self-locking. In other words, by advancing tether 110 through one or both passages, the tension on tether 110 alone results in a tightening, and preferably a locking, of tether 110 in clamping assembly 130.

Preferably, clamping assembly 130 is configured such that tether 110 can be clamped and/or locked in clamping assembly 130 so as to allow tether 110 to move through one or both passages in a first direction to lock the tether in place but so as to prevent, or at least substantially prevent, tether 110 from moving through one or both passages in a second direction opposite from the first direction. Thus, with respect to the view of FIGS. 2A and 2B, tether 110 may be advanced in an upward direction along both opposing passages, thereby resulting in a tether loop (see FIG. 1) that gets smaller, but may be prevented, or at least substantially prevented, from being advanced in a downward direction. Thus, upon applying a force to tether 110 in the upward direction, the loop locks in place, preferably about a spinal feature. In some embodiments, the greater the force applied in a locking direction, the tighter the lock, and therefore the more difficult it is to move the tether in an opposite direction from the locking direction.

In the depicted embodiment, this self-locking feature may be enhanced by providing a friction differential between the two opposing surfaces through which one or more portions of tether 110 are received. Preferably, this friction differential is applied such that a movable surface has a greater surface roughness than an opposing non-movable surface. Because, as discussed in greater detail below, in some implementations of inventive methods disclosed herein, the inner coupling piece 140 may be coupled with a rod 120 or other elongate member prior to coupling outer coupling piece 150 with inner coupling piece 140, outer coupling piece 150 may be considered the "moveable" element of clamping assembly 130.

Thus, for example, as depicted in FIG. 2B, inner surface(s) 152 of outer coupling piece 150 comprises a plurality of projections 153. In some embodiments, projections 153 may be defined by a plurality of elongated grooves formed on the inner surface 152 of outer coupling piece 150. However, alternative embodiments are contemplated in which projections 153 may comprise, for example, teeth. As still another alternative, inner surface 152 of outer coupling piece 150 may, in some embodiments, lack deliberately formed projections and may instead simply comprise a roughened surface. Outer surface(s) 142 of inner coupling piece 140 may, in some embodiments, comprise a smooth surface. However, so long as a friction differential is provided, whether by providing projections 153 or otherwise, outer surface(s) 142 need not be smooth in some embodiments. Surfaces 142 and 152, along with their respective surface features, are therefore an example of means for self-locking a tether within a rod-coupling assembly.

It is also contemplated, however, that in some embodiments, suitable locking may be provided without providing the friction differential described above. For example, the embodiment depicted in FIG. 2B also provides for self-locking of tether 110 by virtue of a wedge-locking feature. Thus, although it may be preferred to have the two opposing surfaces 142/152 have a friction differential, this may be omitted in certain contemplated embodiments. In embodiments in which these two surfaces are identical, or at least substantially identical, it is also preferred that both surfaces be roughened, contoured, and/or formed with frictional features, such as teeth or protrusions, for example. However, it is also contemplated that for certain applications opposing surfaces 142/152 may instead both be smooth.

Because of the unique design of assembly 100, locking of tether 110 may also result in further locking/tightening of the grip on rod 120. For example, due to the wedging of outer coupling piece 150 onto inner coupling piece 140, as the tension on tether 110 is increased in the tightening direction by pulling one or both ends of tether 110 through the two opposing passages defined by outer coupling piece 150 and inner coupling piece 140, not only is tether 110 pinched more tightly therebetween to prevent it from being loosened, but, at the same time, the slot 145 created by the inner surface of inner coupling piece 140 is squeezed against the rod 120 more tightly to further lock the tether clamping assembly 130 in place with respect to the rod 120. This feature is provided for by virtue of the wedge lock previously described, in which two tapering surfaces are wedged against each other (with the tether 110 therebetween) in combination with making the inner coupling piece 140 flexible so that the size of slot 145 can vary to facilitate this compression. Preferably, as shown in the depicted embodiment, these tapering surfaces are frusto-conical surfaces.

Figure 3:
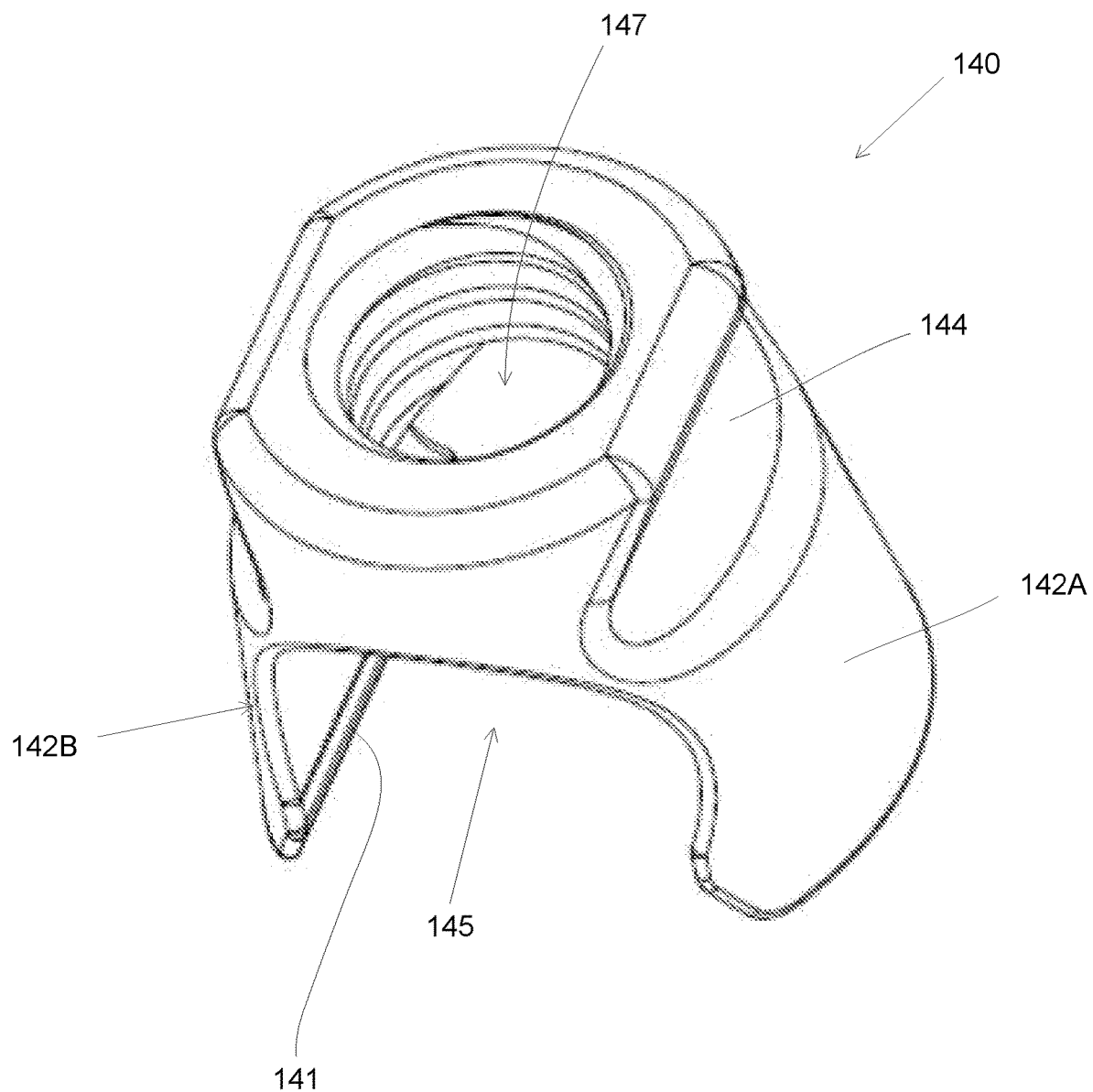
FIG. 3 is a perspective view of an inner coupling piece of a tether clamping assembly according to some embodiments.
Figure 4:
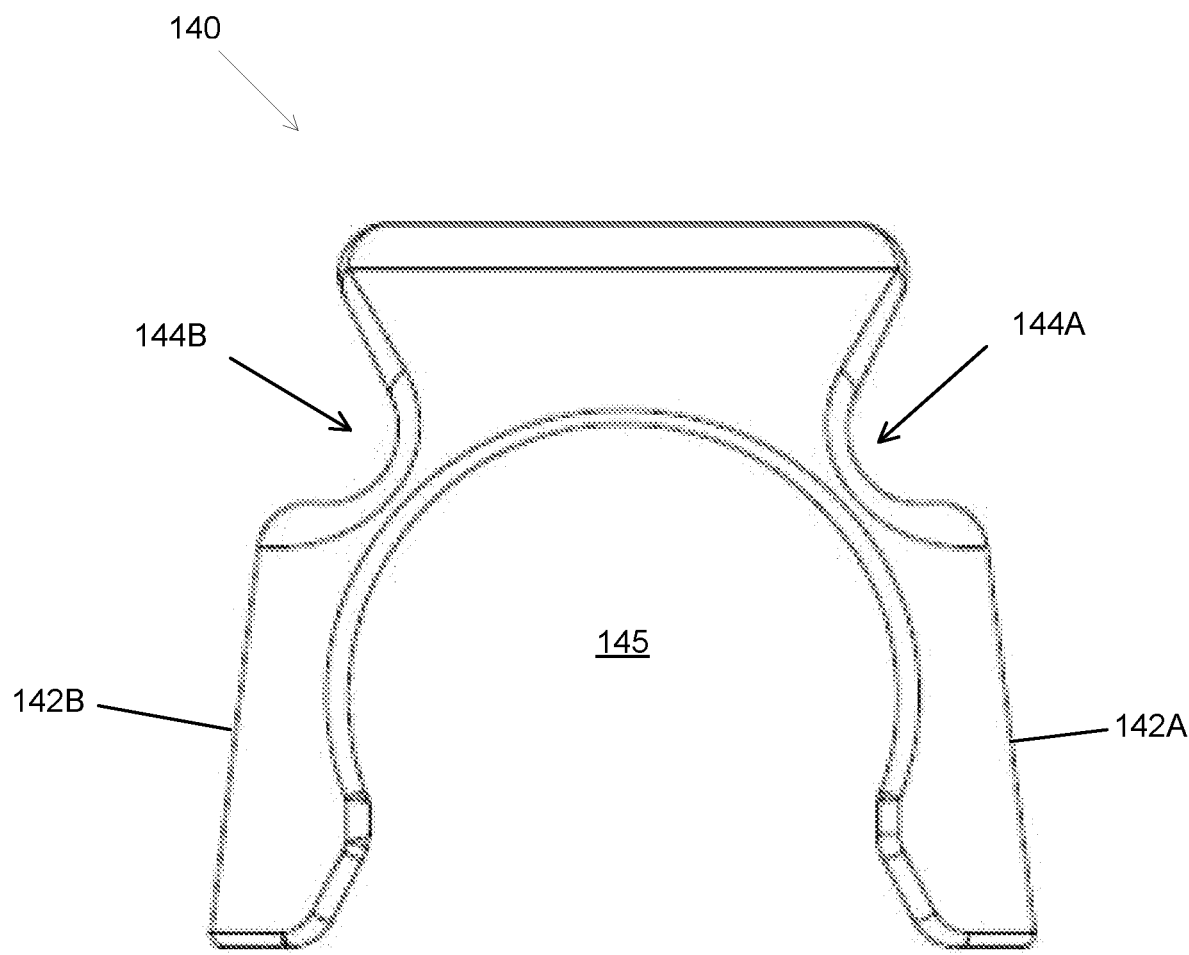
FIG. 4 is a side elevation view of the inner coupling piece of FIG. 3.
Figure 5:
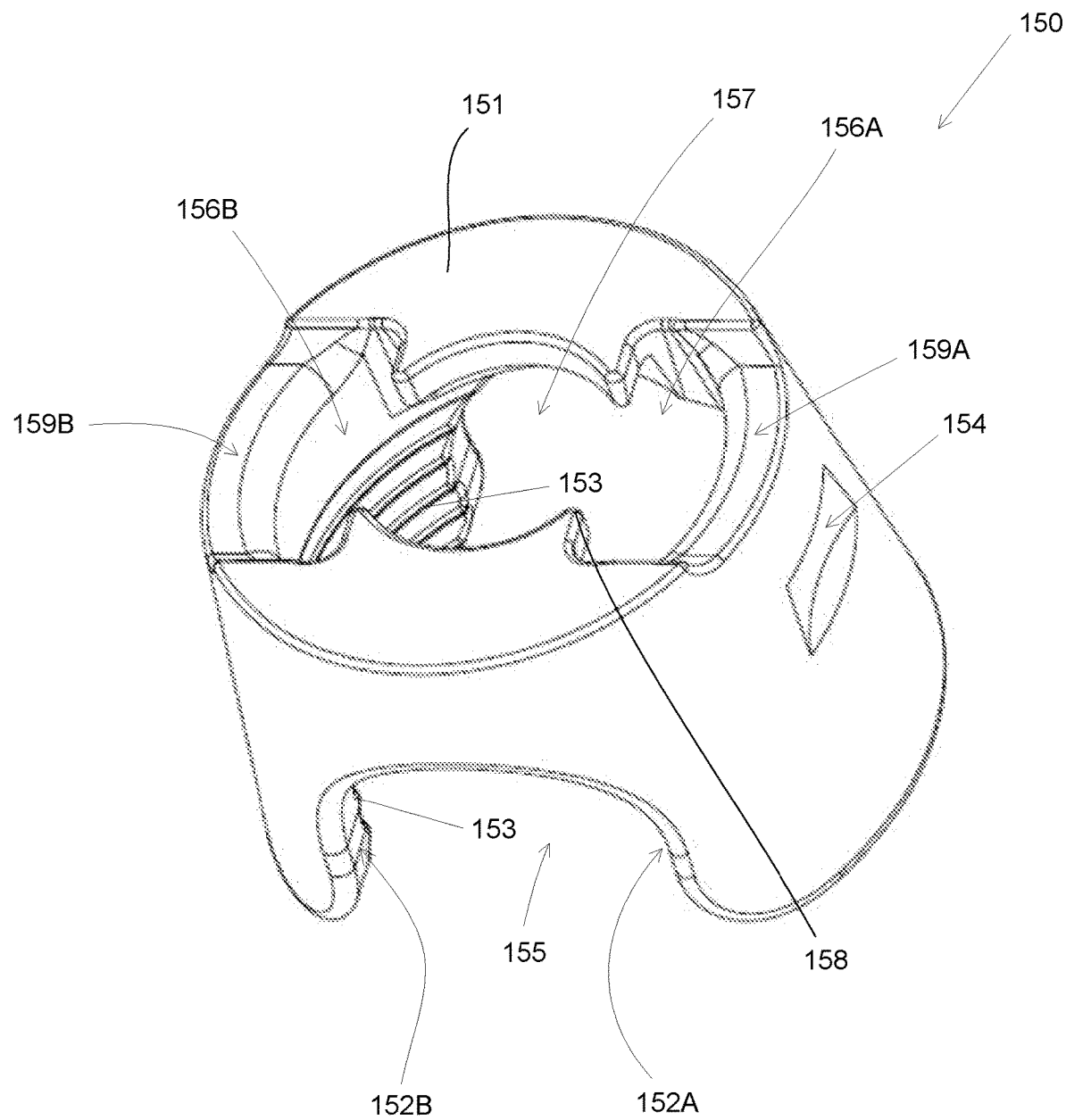
FIG. 5 is a perspective view of an outer coupling piece of a tether clamping assembly according to some embodiments.

Other aspects/features of spinal fixation assembly 100 can be seen in FIGS. 3-8. For example, as shown in FIG. 3, inner coupling piece 140 may comprise a central opening 147, which may be threaded to receive cap 160. Opening 147 may be configured to be aligned with opening 157 of outer coupling piece 150, as shown in FIG. 5, upon coupling of outer coupling piece 150 with inner coupling piece 140. Although preferably openings 147 and 157 are configured to be aligned when outer coupling piece 150 is coupled with inner coupling piece 140, opening 157 need not be threaded since threaded opening 147 may engage cap 160 and thereby engage outer coupling piece 150 without itself requiring a direct threaded connection with cap 160.

In some embodiments, cap 160 may be configured to contact, either directly or indirectly, rod 120, so as to increase the locking force that may be desired thereon. In some such embodiments, the end of the threaded shaft of cap 160 may therefore comprise a spiked tip, one or more grooves, protrusions, or surface roughened features to enhance the grip between cap 160 and rod 120.

Inner coupling piece 140 may further comprise opposing grooves 144. Grooves 144 may be provided in order to increase the flexibility of slot 145. For example, as previously mentioned, slot 145 may be configured to expand to receive rod 120 and then resiliently snap back in place to at least partially envelop rod 120, which functionality may be provided by grooves 144. In some embodiments, grooves 144 may also, or alternatively, be used to provide locations to facilitate gripping/engagement by an instrument that may be used to install coupling piece 140 and/or hold coupling piece 140 in place during one or more stages of a surgical procedure.

As also better seen in FIG. 4, inner coupling piece 140 may comprise opposing outer surfaces 142A and 142B, each of which may partially define a separate tether passage. As previously mentioned, preferably, outer surfaces 142A and 142B are smooth or at least have surface roughnesses that are less than that of respective opposing surfaces, which may be defined by outer coupling piece 150, that, together with outer surfaces 142A and 142B, define opposing tether passages. Similarly, FIG. 4 better depicts opposing grooves 144A and 144B, which directly extend from opposing outer surfaces 142A and 142B, respectively. As best shown in this figure, grooves 144A and 144B, together with slot 145, form opposing narrowed portions that provide the aforementioned flexibility and/or provide engagement locations for a suitable instrument.

FIG. 5 is a perspective view of outer coupling piece 150. As best seen in this figure, the upper portion of outer coupling piece 150 may comprise one or more features to facilitate desired functionality. For example, as previously mentioned an opening 157 may be provided to receive a threaded projection or another projection from a cap and/or set screw. In addition, opening 157 need not be threaded, but may be defined by a plate 151 configured to engage a portion of inner coupling piece 140 that defines a threaded opening 147 configured to be aligned with opening 157 such that inner coupling piece 140 can extend into but cannot extend out of the opposite end of outer coupling piece 150. Plate 151 may also be configured to provide a surface upon which a flanged portion 164 of cap 160 may rest and/or pinch a portion of tether 110, as discussed in greater detail below.

Plate 151 may further define opposing tether openings 156A and 156B. In embodiments using a tether having an elongated, rectangular cross-section, such as tether 110, tether openings 156A and 156B may have a similar matching shape such that the tether may snap into place when properly oriented within the opposing passages, the openings at one end of which are defined by tether openings 156A and 156B.

Tether openings 156A and 156B may be partially defined by four corners 158 that are positioned along the portion of outer coupling piece 150 defining opening 157. Corners 158 are defined by opening 157 along with respective walls that extend parallel to slit 155 (and therefore extend parallel to an axis defined by a rod positioned therein). These tether openings 156A/156B may be useful in allowing the tether to be held in place temporarily (before locking/clamping) to allow a practitioner to perform other tasks while awaiting finalization of the installation/surgery.

Figure 8:
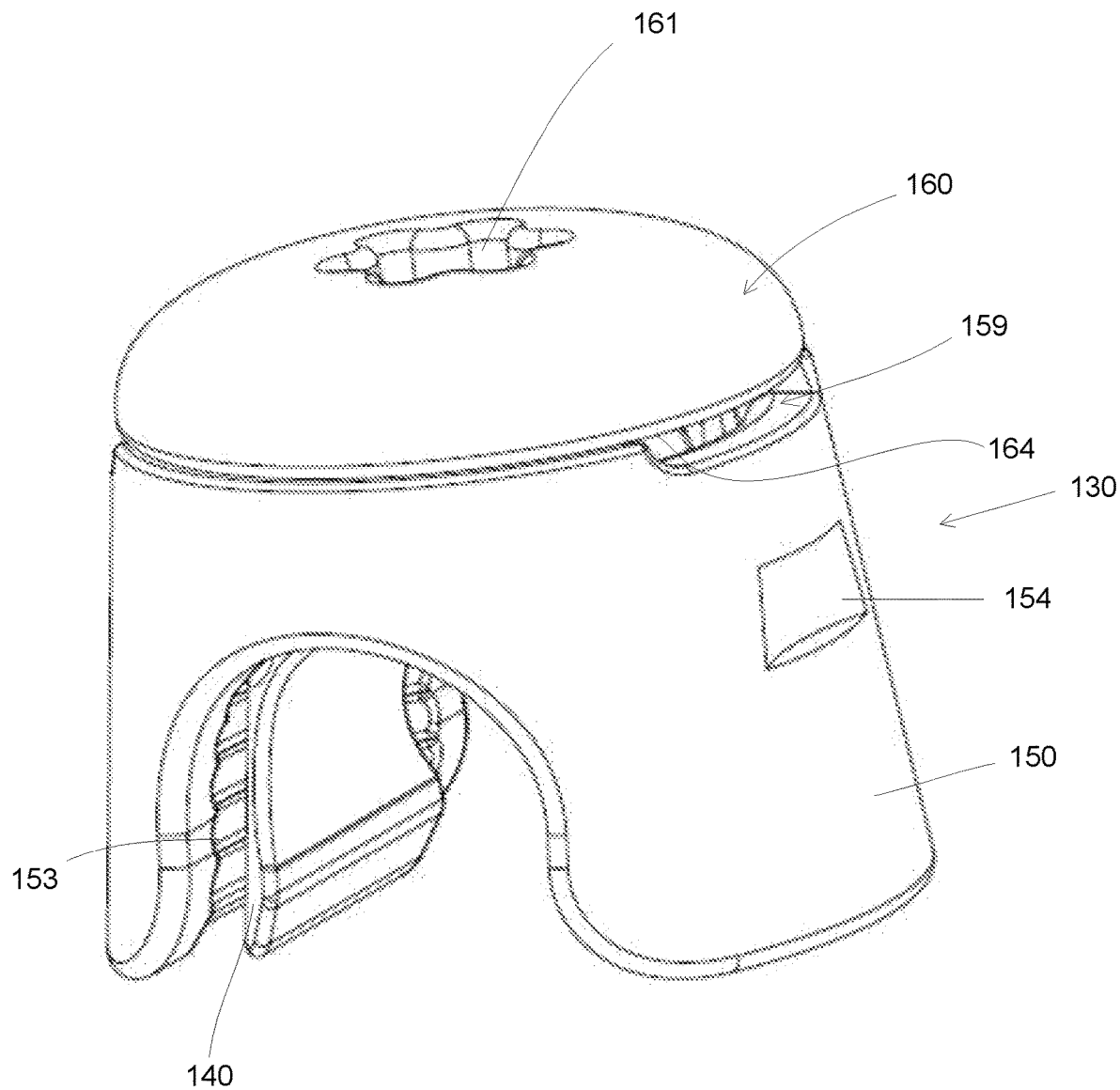
FIG. 8 is a perspective view of a tether clamping assembly according to some embodiments.

As also shown in FIG. 5, opposing slits 159A and 159B may be formed adjacent to plate 151. As best seen in FIG. 8, which depicts assembly 130 with cap 160 in place, slits 159A and 159B may, together with flanged portion 164 of cap 160, define opposing apertures through which opposing portions of tether 110 may exit from opposing sides of assembly 130.

Some embodiments may further comprise one or more features to facilitate engagement with a suitable instrument. Thus, for example, outer coupling piece 150 comprises a notch 154, which may engage a corresponding protruding element of a suitable surgical instrument. Although not visible in FIG. 5, in some embodiments, a similar notch may be formed on the opposite side of outer coupling piece 150.

Figure 6:
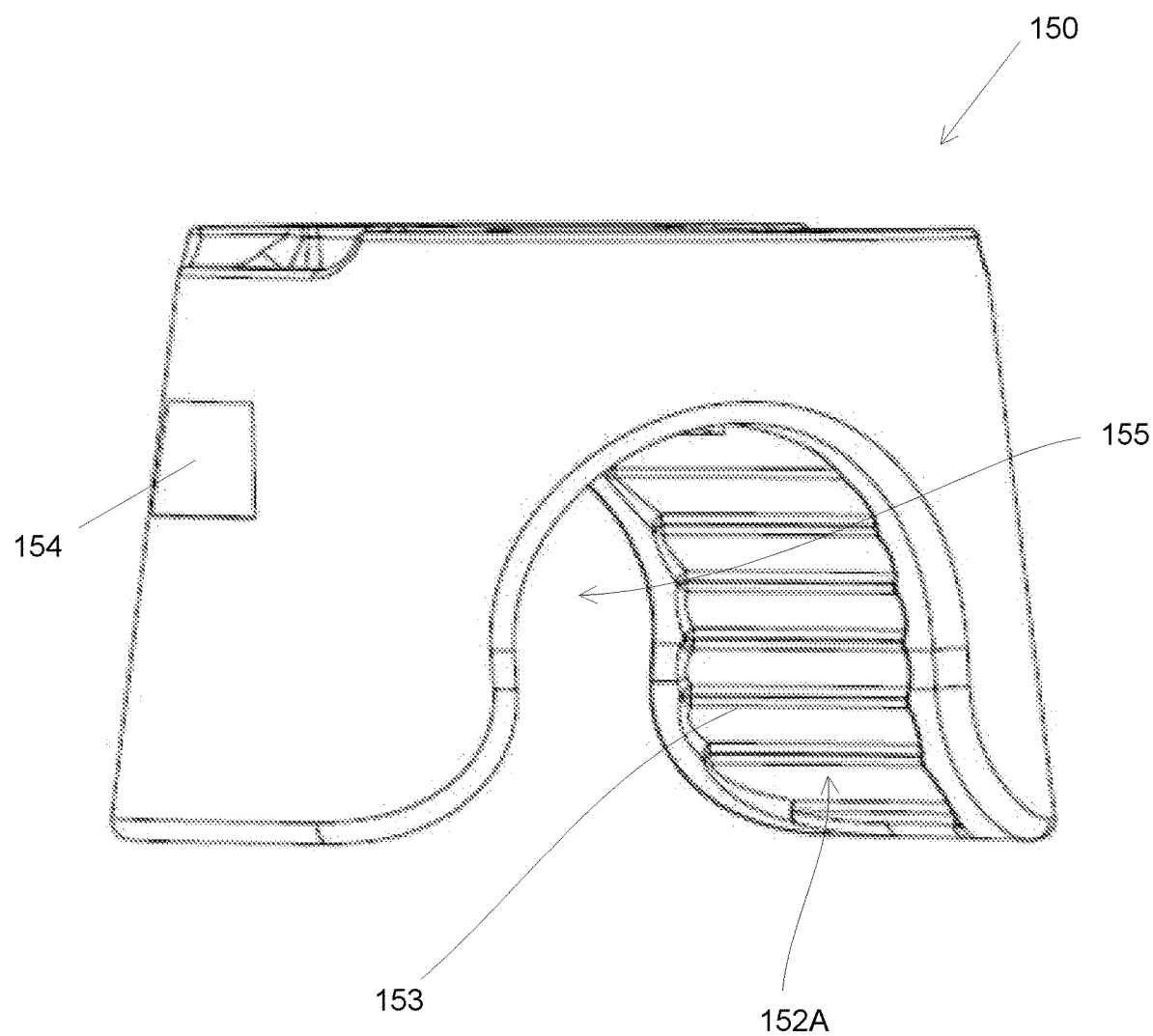
FIG. 6 is a side elevation view of the outer coupling piece of FIG. 5.

FIG. 6 more clearly depicts projections 153 formed within curved inner surface 152A of outer coupling piece 150. As shown in this figure, projections 153 may be formed by cutting elongated, parallel grooves within inner surface 152A. Although not visible in FIG. 6, as previously mentioned, in preferred embodiments, the opposing inner surface similarly comprises a plurality of projections 153 to facilitate the self-locking feature of assembly 130.

Figure 7:
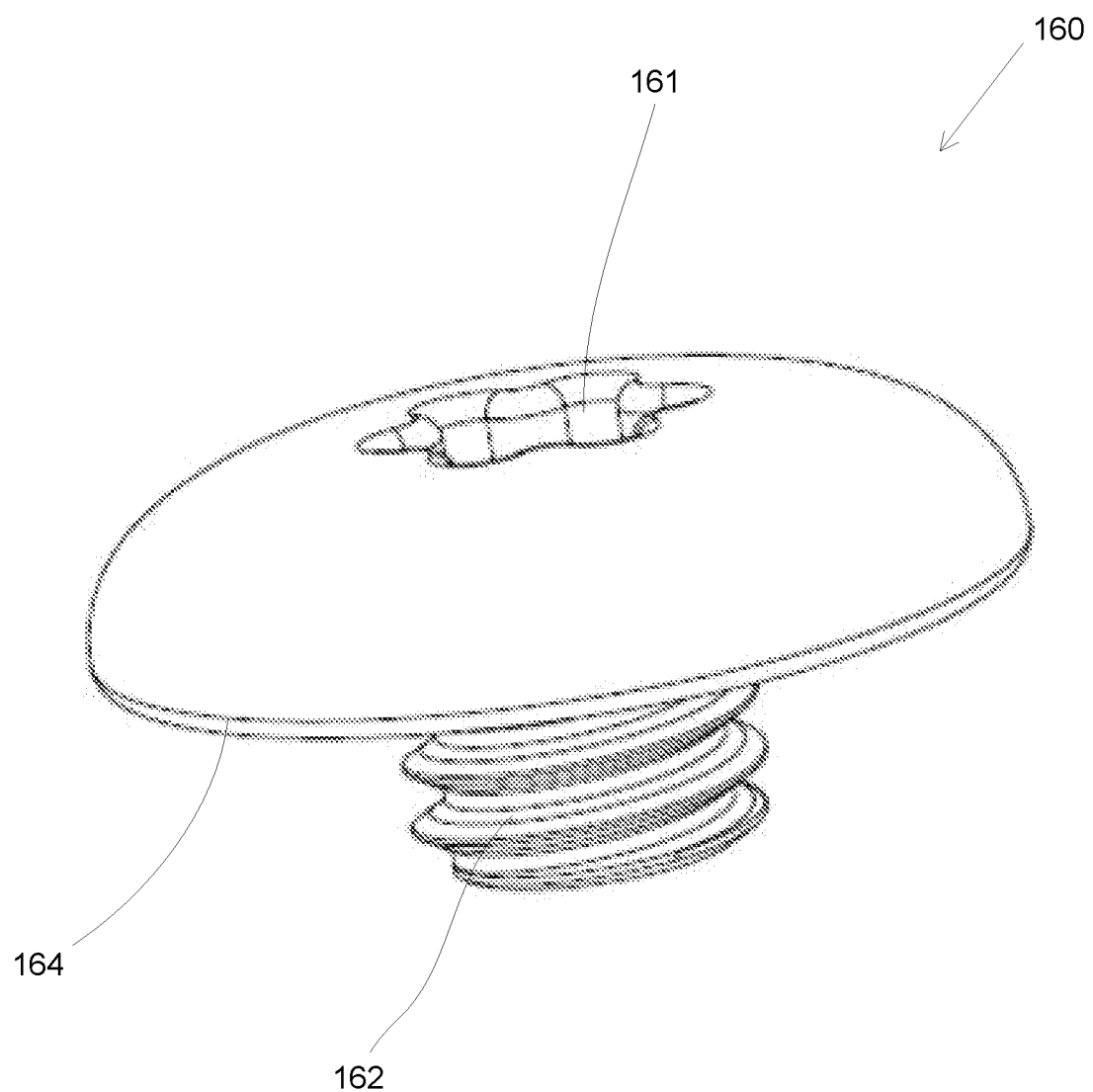
FIG. 7 is a perspective view of a threaded cap that may be used in connection with one or more of the tether clamping assemblies disclosed herein.

FIG. 7 is a perspective view of a cap 160 of spinal fixation assembly 100 according to some embodiments. Cap 160 comprises a flanged portion 164, which may be configured to engage an upper surface of outer coupling piece 150, such as plate 151. Cap 160 further comprises a male threaded portion 162 and a keyed slot 161. As previously mentioned, male threaded portion 162 may be configured to engage female threads of inner coupling piece 140 and outer coupling piece 150 may be clamped therebetween. Keyed slot 161 may be configured to engage an instrument, such as a driver, used to couple cap 160 to assembly 130.

In some embodiments, a portion or, in some such embodiments, two opposing portions, of the tether 110 may be clamped in between flanged portion 164 of cap 160 and another portion of assembly 130, such as the ledges formed by opposing slits 159A and 159B or plate 151 of outer coupling piece 150. Thus, cap 160 is an example of secondary means for locking a tether within a rod-coupling assembly. Cap 160 may also serve the function of increasing the lock on the rod and/or tether and/or decreasing the possibility of unwanted loosening/disassembly.

In addition, providing cap 160 may decrease the possibility of frayed portions of tether 110 from extending down into assembly 130 following cutting of tether 110. This may allow for cutting of tether 110 closer to assembly 130 than may otherwise be possible or desirable. However, as previously explained, self-locking may be provided by the differential friction of the opposing surfaces of one or both tether passages of tether clamping assembly 130. Thus, it is contemplated that cap 160 may be omitted in some embodiments. It is also contemplated that cap 160 may comprise a set screw lacking a flanged portion in some embodiments.

FIG. 8 is a perspective view of tether clamping assembly 130 showing inner coupling piece 140 fully inserted within outer coupling piece 150 and with cap 160 fully engaged with inner coupling piece 140. Although normally a tether would be engaged between opposing surfaces of inner coupling piece 140 and outer coupling piece 150, respectively, in this configuration, tether 110 is omitted from FIG. 8 to allow for better viewing of certain aspects of assembly 130. Most notably, opposing apertures are depicted that may allow for a tether to exit from opposite sides of assembly 130. These apertures are defined by opposing slits 159 (only one of which is visible in FIG. 8), respectively, along with a lower surface of flanged portion 164 of cap 160.

Another unique aspect of assemblies 100 and/or 130 is the ability to loosen the grip/lock/clamp on the tether 110 for readjustment. As previously mentioned, locking of the tether may be accomplished automatically by engaging the tether 110 between the opposing surfaces of the inner and outer coupling pieces and pulling the tether through one or both of the openings in the locking direction, with the optional cap 160 to further enhance this locking of the tether 110 and/or the rod 120. This may allow for sequential tightening of various elements of a spinal fixation system without leaving instrumentation in place while moving to a new location within the system, which may also reduce the instrument tray and decrease surgery time.

If loosening is needed, in preferred embodiments, due to the unique features described herein, the tether may be loosened by simply pulling or otherwise tensioning one or both of the free ends of the tether. In the event that the clamp provided by the inner and outer coupling pieces is too tight, such as when a locking cap/nut has been applied, in some embodiments and implementations the outer coupling piece 150 may be engaged, likely with a suitable instrument, in order to lift the outer coupling piece 150 away from the inner coupling piece 140 slightly, which will release the lock on tether 110 and allow the tether 110 to be loosened. In some embodiments, notch 154 may be configured to engage a corresponding element of a suitable surgical instrument in order to facilitate this loosening.

Figure 9:
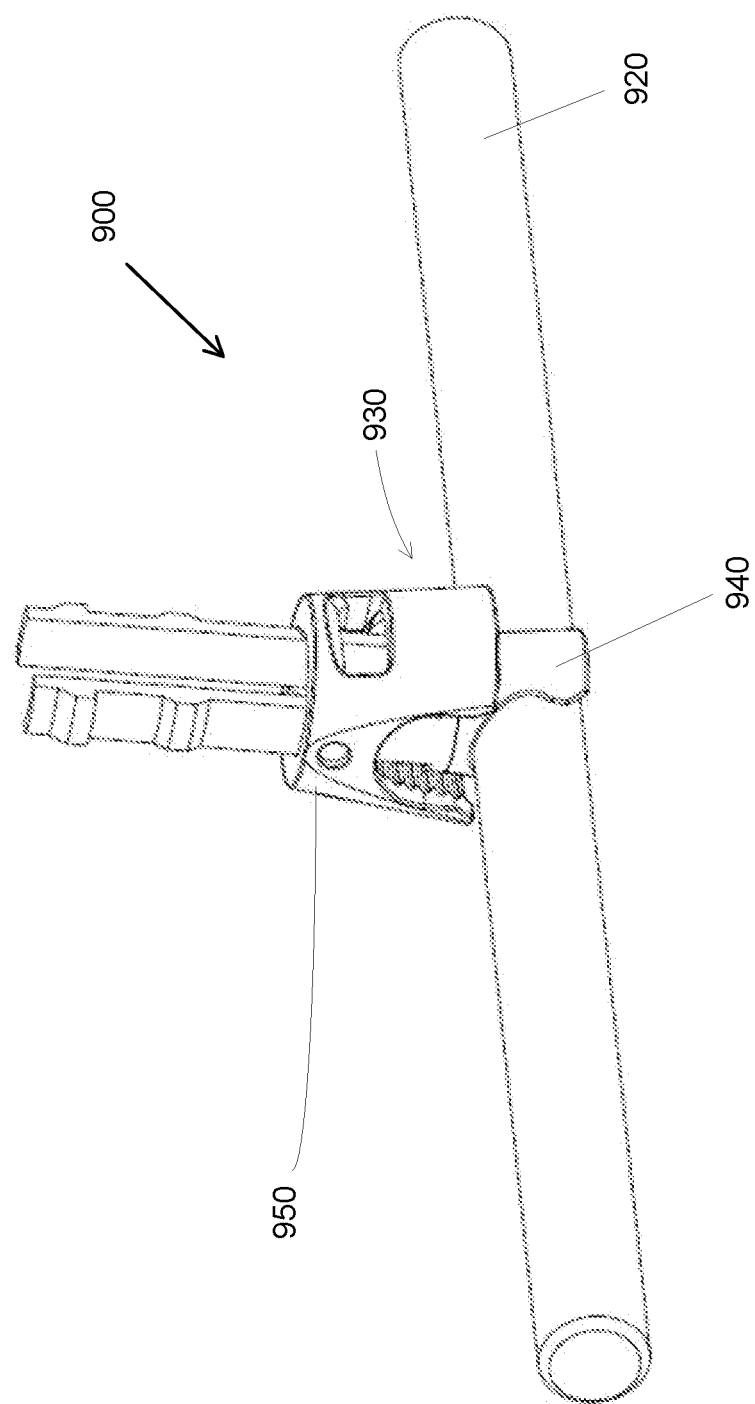
FIG. 9 is a perspective view of a spinal fixation assembly including a tether clamping assembly according to another embodiment.

FIG. 9 is a perspective view of an alternative embodiment of a spinal fixation assembly 900. Although not depicted in FIG. 9, assembly 900 would typically comprise a tether, which may be similar to tether 110, that is configured to engage a spinal feature of a patient's spine, such as, in preferred embodiments, looped around the spinal lamina and/or other spinal features, such as the transverse processes of the patient's spine.

Like assembly 100, assembly 900 further comprises a tether clamping assembly 930 configured to engage and couple a coupling member, such as a rod 920 or other elongate member, with a tether so as to facilitate coupling of a patient's spine in a desired position without use of pedicle screws or other similar bone-invasive components. Tether clamping assembly 930 again comprises two separate elements configured to be coupled with one another so as to clamp one or more (preferably two) portions of a tether therein. More particularly, tether clamping assembly 930 comprises an inner coupling piece 940 configured to be received within an outer coupling piece 950.

Figure 10:
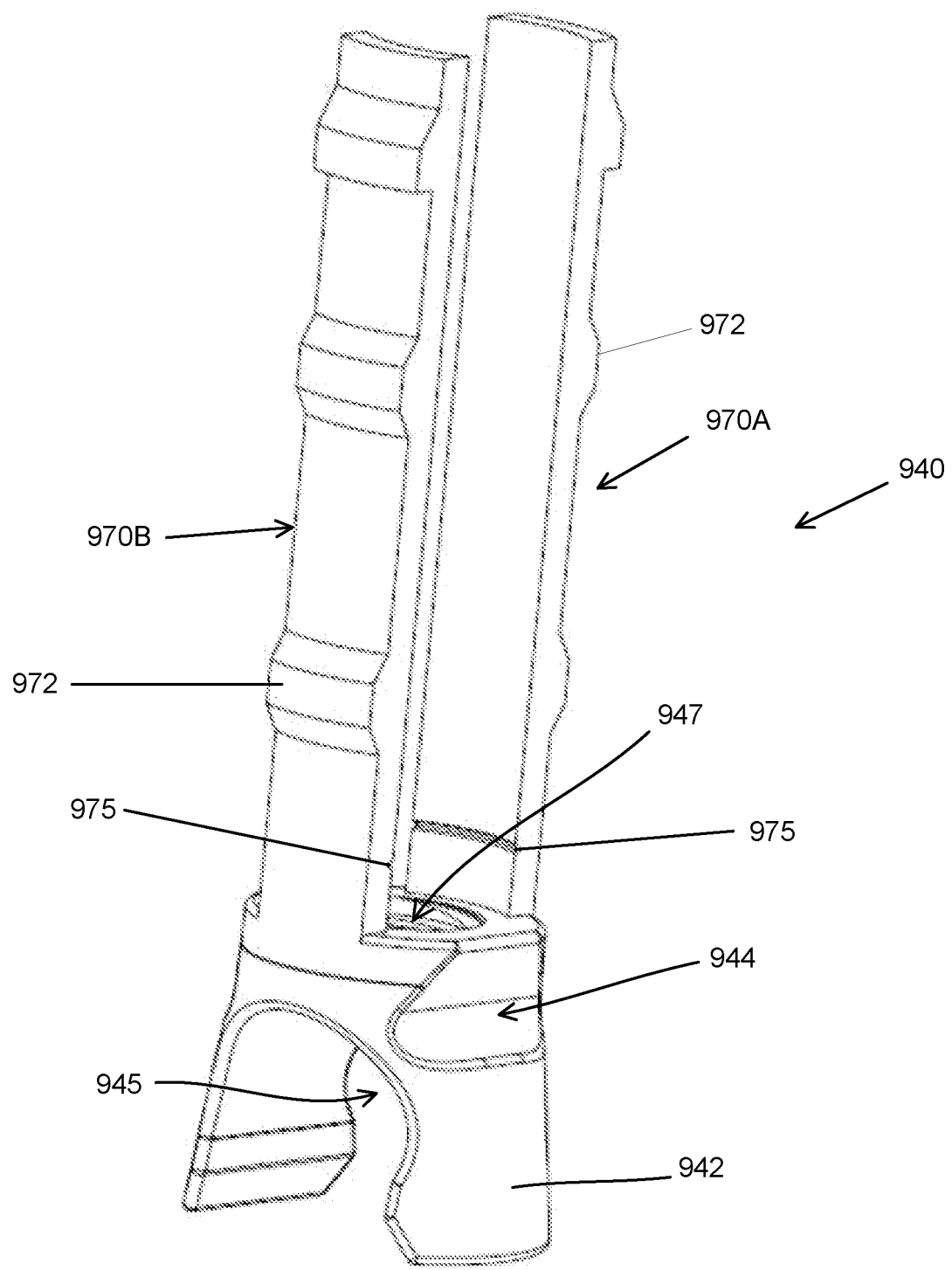
FIG. 10 is a perspective view of the inner coupling piece of the tether clamping assembly of FIG. 9.

However, tether clamping assembly 930 differs from tether clamping assembly 130 in several ways. For example, as shown in FIGS. 9 and 10, inner coupling piece 940 comprises a pair of removable tabs, namely, tabs 970A and 970B. Tabs 970A and 970B may be configured to facilitate coupling of outer coupling piece 950 with inner coupling piece 940. Tabs 970A and 970B may comprise a plurality of ridges 972.

Each ridge 972, or each pair of adjacent ridges 972, may serve a distinct purpose during the installation process. For example, the top pair of ridges 972 may be used to prevent the outer coupling piece 950 from being removed from assembly 930 during, for example, snapping of the rod 920 into slot 945. The middle pair of ridges 972 may prevent the outer coupling piece 950 from dropping all of the way down adjacent to the threaded opening 947 of inner coupling piece 940 to provide spacing for an instrument or a surgeon's hand during this stage.

Following this stage, the outer coupling piece 950 may be dropped down below the lowest pair of ridges to allow for threading of the tether through opposing passages defined by respective inner surfaces of the outer coupling piece 950 and respective, opposing outer surfaces of the inner coupling piece 940, as previously described. After threading the tether through these passages, the tether may be tensioned about a spinal feature and/or bone.

As previously mentioned, preferably tether clamping assembly 930 is configured to provide for self-locking of the tether. In other words, in some embodiments, the tether clamping assembly 930 may be configured such that the tether can be clamped in between opposing surfaces so as to allow the tether to move through the passage(s) in a first direction and lock the tether in place so as to, without any further steps or locking elements/features, at least substantially prevent the tether from moving through the passage(s) in a second direction opposite from the first direction. As also previously mentioned, this self-locking feature may be provided by providing a friction differential between the two opposing surfaces through which one or more portions of the tether are received. Preferably, this friction differential is applied such that a movable surface has a greater surface roughness than an opposing non-movable surface.

Figure 11:
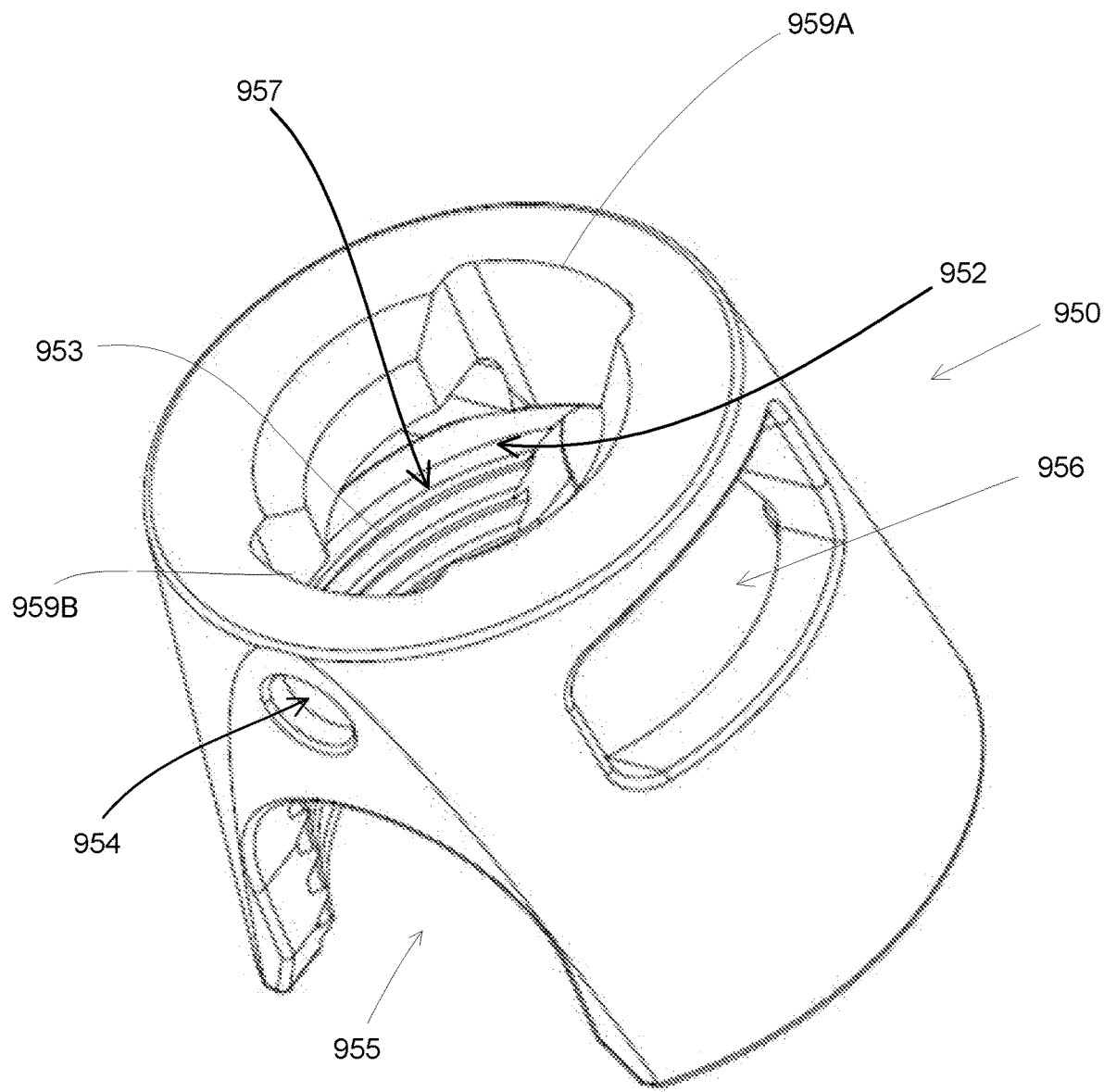
FIG. 11 is a perspective view of the outer coupling piece of the tether clamping assembly of FIG. 9.

Thus, for example, as depicted in FIGS. 10 and 11, opposing inner surface(s) 952 of outer coupling piece 950 comprises a plurality of projections 953, which may be formed by elongated grooves. Outer surface(s) 942 of inner coupling piece 940 may, in some embodiments, comprise a smooth surface, or at least a surface lacking projections/grooves. However, again, so long as a friction differential is provided, whether by providing projections 953 or otherwise, outer surface(s) 942 need not necessarily be smooth. Surfaces 942 and 952, along with their respective surface features, are therefore another example of means for self-locking a tether within a rod-coupling assembly.

Once the tether has been suitably tensioned and locked in place, tabs 970A and 970B may be removed. In order to facilitate such removal, weakened portions 975, such as frangible weakening lines, may be formed in one or both of tabs 970A and 970B. Inner coupling piece 940 may also comprise opposing grooves 944 for increasing the flexibility of slot 945 and/or facilitate gripping/engagement by a surgical instrument.

Like outer coupling piece 150, outer coupling piece 950 comprises an opening 957, which may be configured to receive a threaded projection or another projection from a cap and/or set screw. Opening 957 need not be threaded but may be configured to be aligned with a threaded opening 947 of inner coupling piece 940, as previously described. Outer coupling piece 950 may further comprise one or more notches 954, which may engage a corresponding protruding element of a suitable surgical instrument.

However, outer coupling piece 950 differs from outer coupling piece 150 in several respects. For example, opposing apertures 956 are formed in outer coupling piece (only one of which is visible in FIG. 11) such that a tether (not shown) may extend through the opposing passages previously mentioned and, instead of exiting from an upper surface, may extend through opposing apertures 956 formed in side walls of outer coupling piece 950.

In addition, instead of comprising opposing slits 159A and 159B in a top surface of the outer coupling piece, as is the case in outer coupling piece 150, outer coupling piece 950 comprises opposing slits 959A and 959B formed in an inner surface of outer coupling piece 950. Opposing slits 959A and 959B may be configured to partially accommodate ridges 972. However, in order to secure outer coupling piece 950 in a desired position on tabs 970A/970B, preferably slits 959A/959B are slightly smaller than ridges 972 such that ridges 972 prevent passage of outer coupling piece 950. Passage of outer coupling piece 950 beyond a given set of ridges 972 may be accomplished by, for example, flexing tabs 970A/970B.

Figure 12:
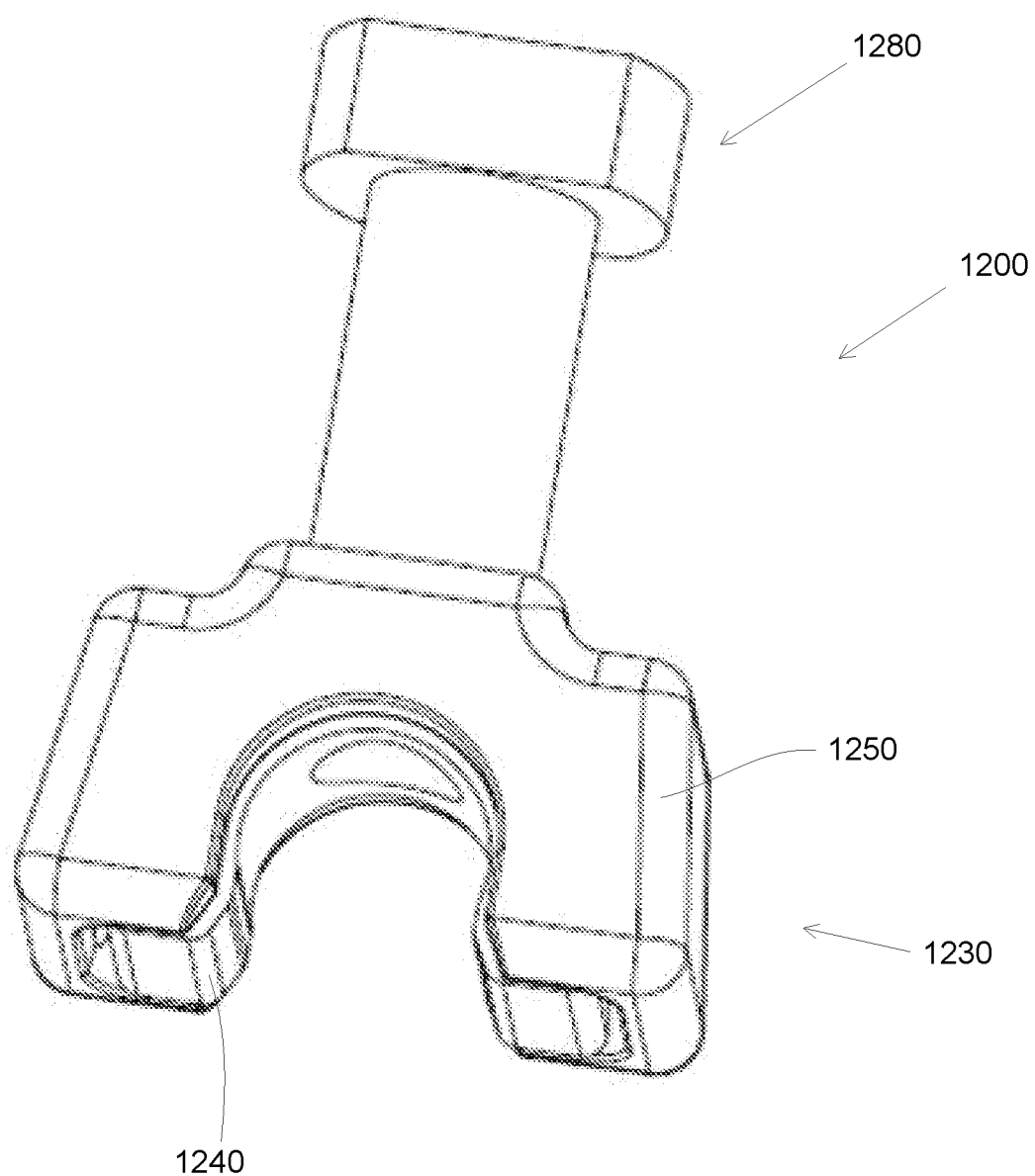
FIG. 12 is a perspective view of a tether clamping assembly according to still another embodiment.

FIG. 12 depicts yet another alternative embodiment of a spinal fixation assembly 1200. Although not depicted in FIG. 12, assembly 1200 would typically comprise a tether, which may be similar to tether 110, that is configured to engage a spinal feature of a patient's spine, and an elongated fixation member or other coupling member, such as a rod.

Like assemblies 100 and 900, assembly 1200 comprises a tether clamping assembly 1230 comprising two separate elements configured to be coupled with one another so as to clamp one or more (preferably two) portions of a tether and rod or another coupling member therein. More particularly, tether clamping assembly 1230 comprises an inner coupling piece 1240 configured to be received within an outer coupling piece 1250, as previously described.

However, tether clamping assembly 1230 differs from the tether clamping assemblies previously described in several ways. For example, as shown in FIGS. 12 and 15, tether clamping assembly 1230 comprises an alignment insert 1280 that is configured to be received within an opening formed within outer coupling piece 1250 and/or inner coupling piece 1240. Alignment insert 1280 may be used to facilitate coupling of outer coupling piece 1250 with inner coupling piece 1240 and/or may be used to facilitate introduction of a set screw (not shown) into inner coupling piece 1240. Thus, alignment insert 1280 may comprise a tip 1282, which may be configured with a smaller diameter relative to an adjacent body portion 1284 so as to allow for receipt of tip 1282 within one or both of threaded opening 1247 of inner coupling piece 1240 (see FIG. 13) and opening 1257 of outer coupling piece 1250 (see FIG. 14). Opposite from tip 1282 is a handle 1286, which may be configured to allow a surgeon or practitioner to push alignment insert 1280 into one or more receiving openings to facilitate introduction and coupling of a set screw into threaded opening 1247. A central bore 1285 may be formed in alignment insert 1280 and may extend from handle 1286 to tip 1282 to allow for a set screw to travel therethrough. A suitable instrument may also be received within bore 1285 to further facilitate such coupling.

Figure 13:
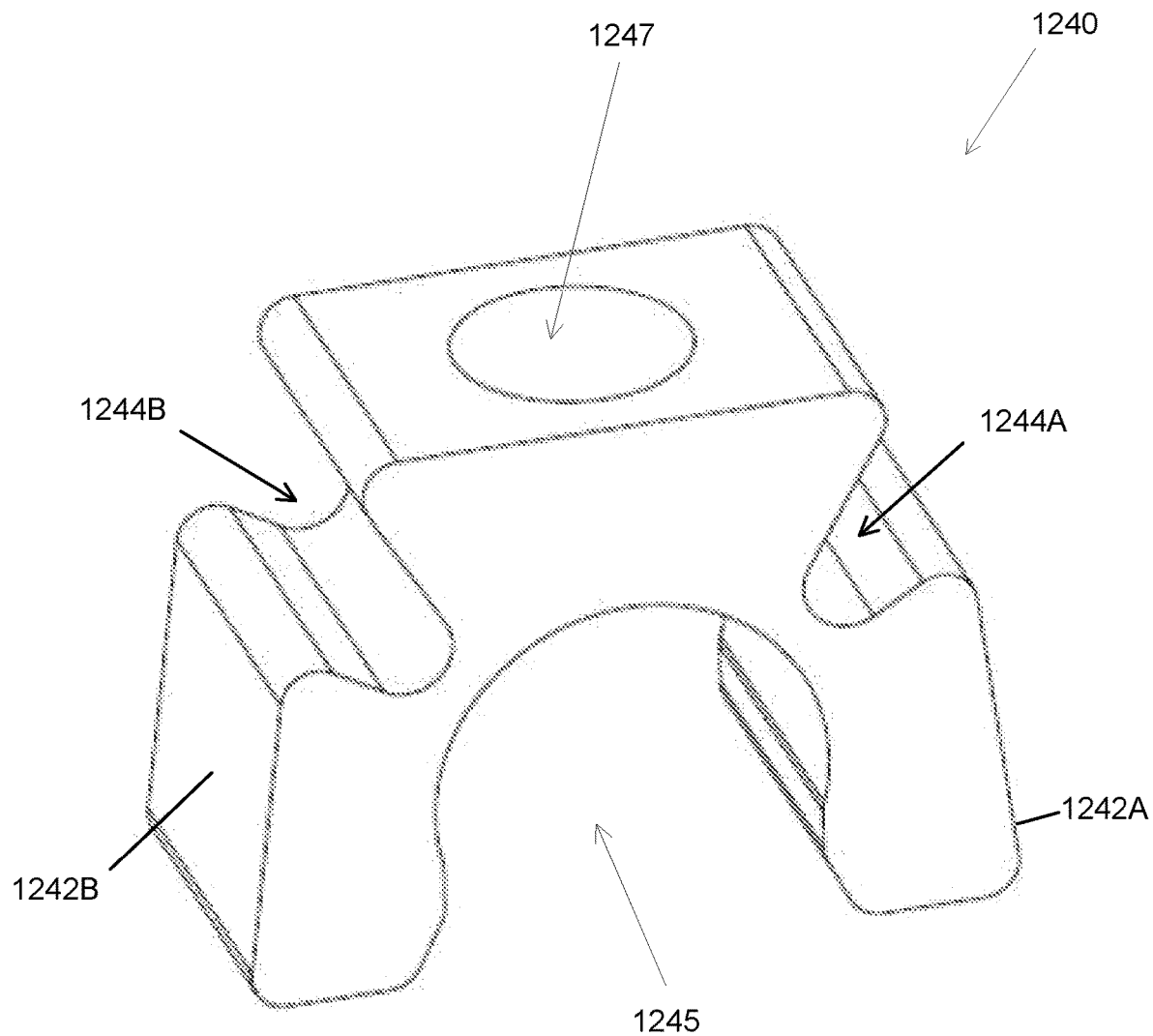
FIG. 13 is a perspective view of the inner coupling piece of the tether clamping assembly of FIG. 12.

A perspective view of the inner coupling piece 1240 is shown in FIG. 13. As shown in this figure, inner coupling piece 1240 comprises a pair of opposing outer surfaces, namely surfaces 1242A and 1242B. As previously discussed, surfaces 1242A and 1242B, respectively, may be configured to define one side of a passage for receipt of a tether (not shown) therethrough. As also previously discussed, surfaces 1242A and 1242B are preferably smooth, or at least having a surface roughness that is less than that of the opposing surface(s), which may be defined by an inner surface or surfaces of outer coupling piece 1250.

As also previously discussed, inner coupling piece 1240 may comprise a slot 1245 that is shaped to match, or at least substantially match, the shape of the outer surface of a rod such that the rod may be firmly engaged/gripped by slot 1245. In some embodiments, slot 1245 may comprise a plurality of teeth (not shown) or a contoured and/or roughened surface to further facilitate a firm engagement between the rod and inner coupling piece 1240. Inner coupling piece 1240 further comprises a pair of opposing grooves, namely, grooves 1244A and 1244B, which may increase the flexibility of slot 1245 to allow for receipt of a rod therein by way of a snap-fit connection. In the depicted embodiment, grooves 1244A and 1244B comprise slits that terminate adjacent to slot 1245.

Figure 14:
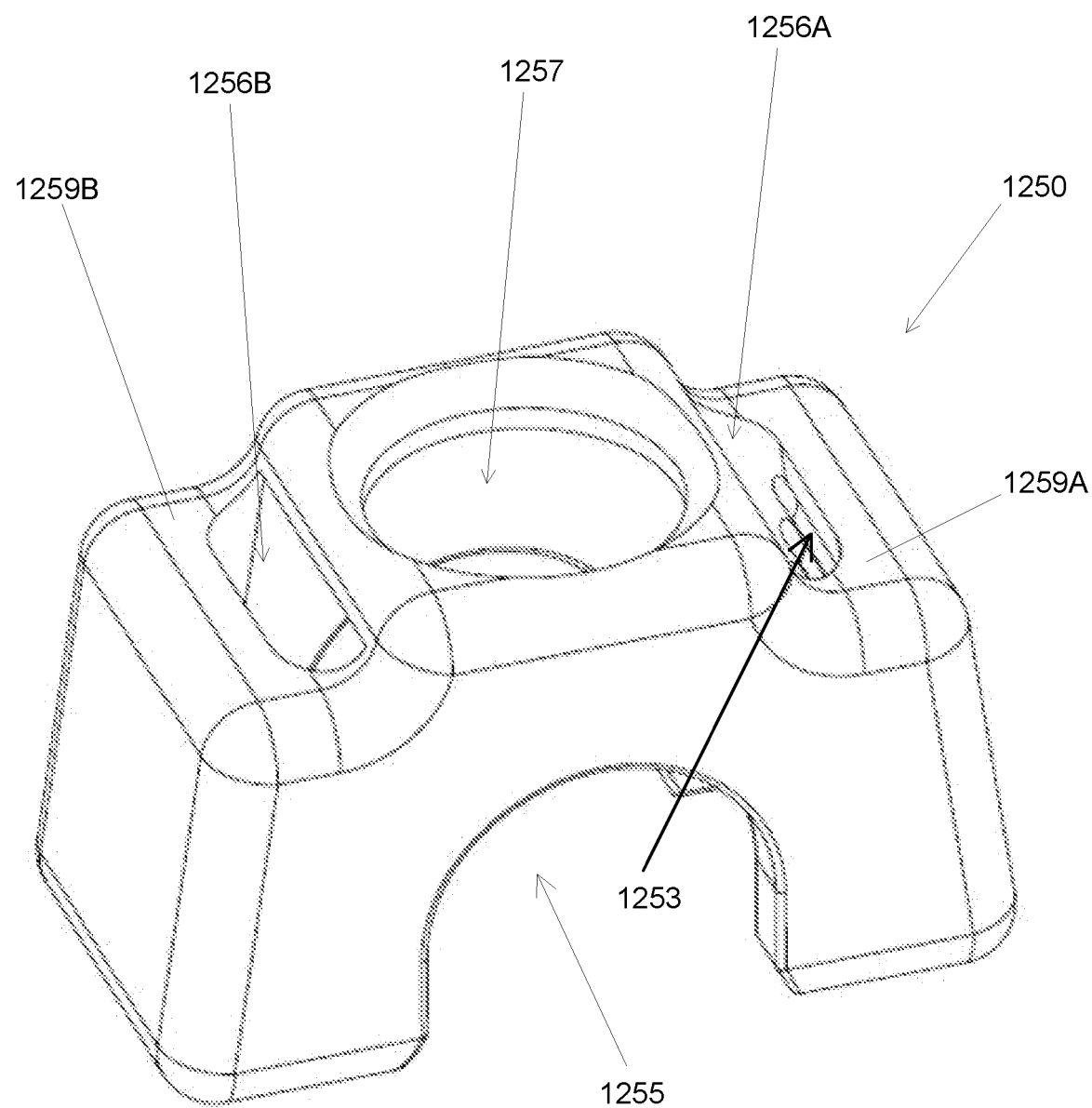
FIG. 14 is a perspective view of the outer coupling piece of the tether clamping assembly of FIG. 12.
Figure 15:
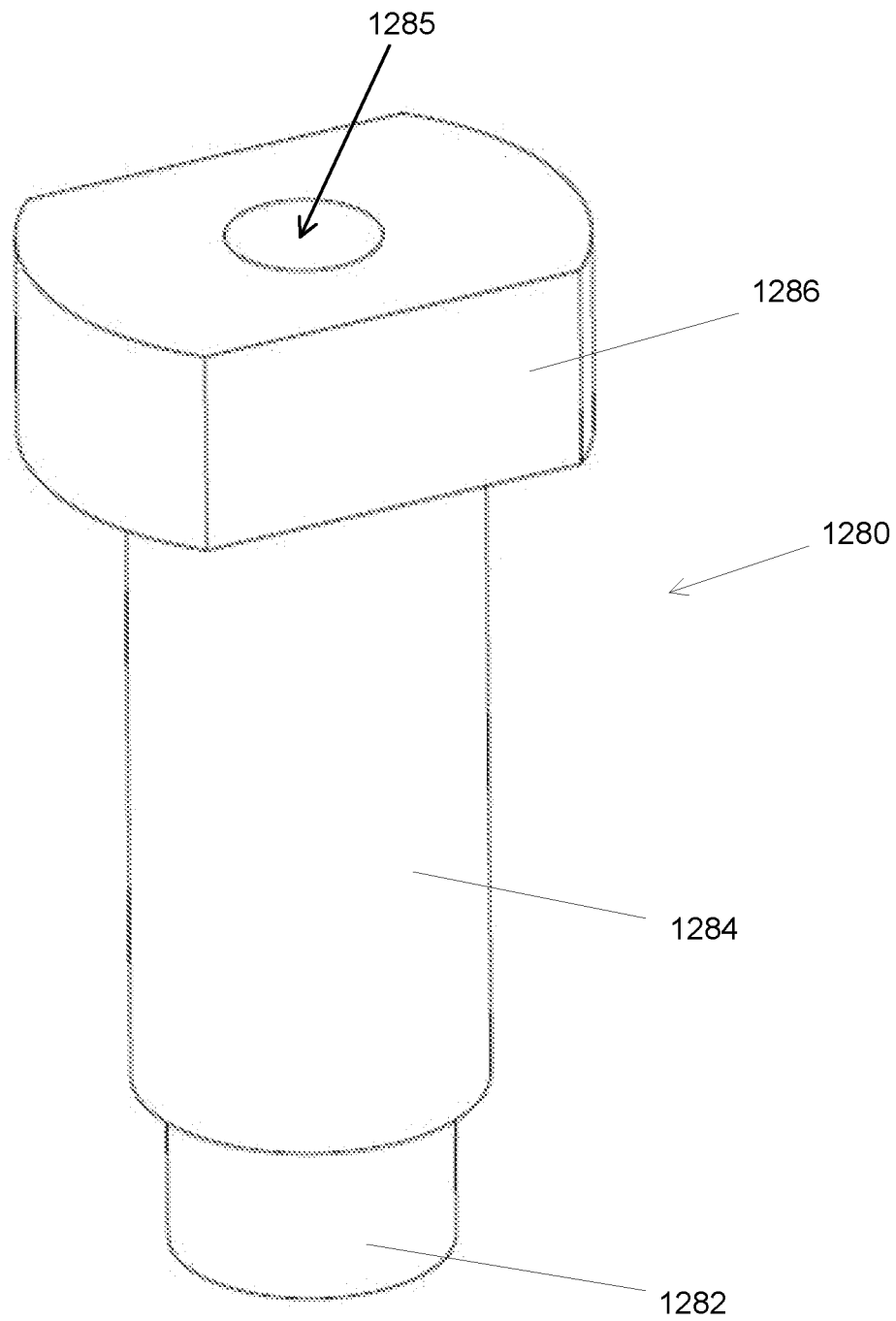
FIG. 15 is a perspective view of an alignment insert configured to be used in connection with the tether clamping assembly of FIG. 12.

A perspective view of outer coupling piece 1250 is shown in FIG. 14. As shown in this figure, outer coupling piece 1250, like inner coupling piece 1240, may comprise a slot 1255 that may be aligned with slot 1245 such that a rod (not shown) or another coupling member may extend through a slot defined by slots 1245 and 1255.

As also shown in FIG. 14, opposing apertures 1256A and 1256B are formed in outer coupling piece 1250 such that a tether (not shown) may extend through the opposing passages previously mentioned and ultimately extend through opposing apertures 1256A and 1256B. Apertures 1256A and 1256B are formed in opposing shelves 1259A and 1259B of outer coupling piece 1250. Shelves 1259A and 1259B may be configured to be aligned, or at least substantially aligned, with the top surface of inner coupling piece 1240 upon fully coupling outer coupling piece 1250 with inner coupling piece 1240.

Finally, as previously discussed, outer coupling piece 1250 further comprises two internal surfaces each having a plurality of projections 1253, which may, in some embodiments, be defined by a series of parallel grooves, as previously described. These surfaces, together with outer surfaces 1242A and 1242B of inner coupling piece 1240, define two separate passages for receipt of opposing portions of a tether therethrough, as also previously described. The opposing surfaces that define these two passages, along with their respective surface features, are therefore another example of means for self-locking a tether within a rod-coupling assembly.

Figure 16:
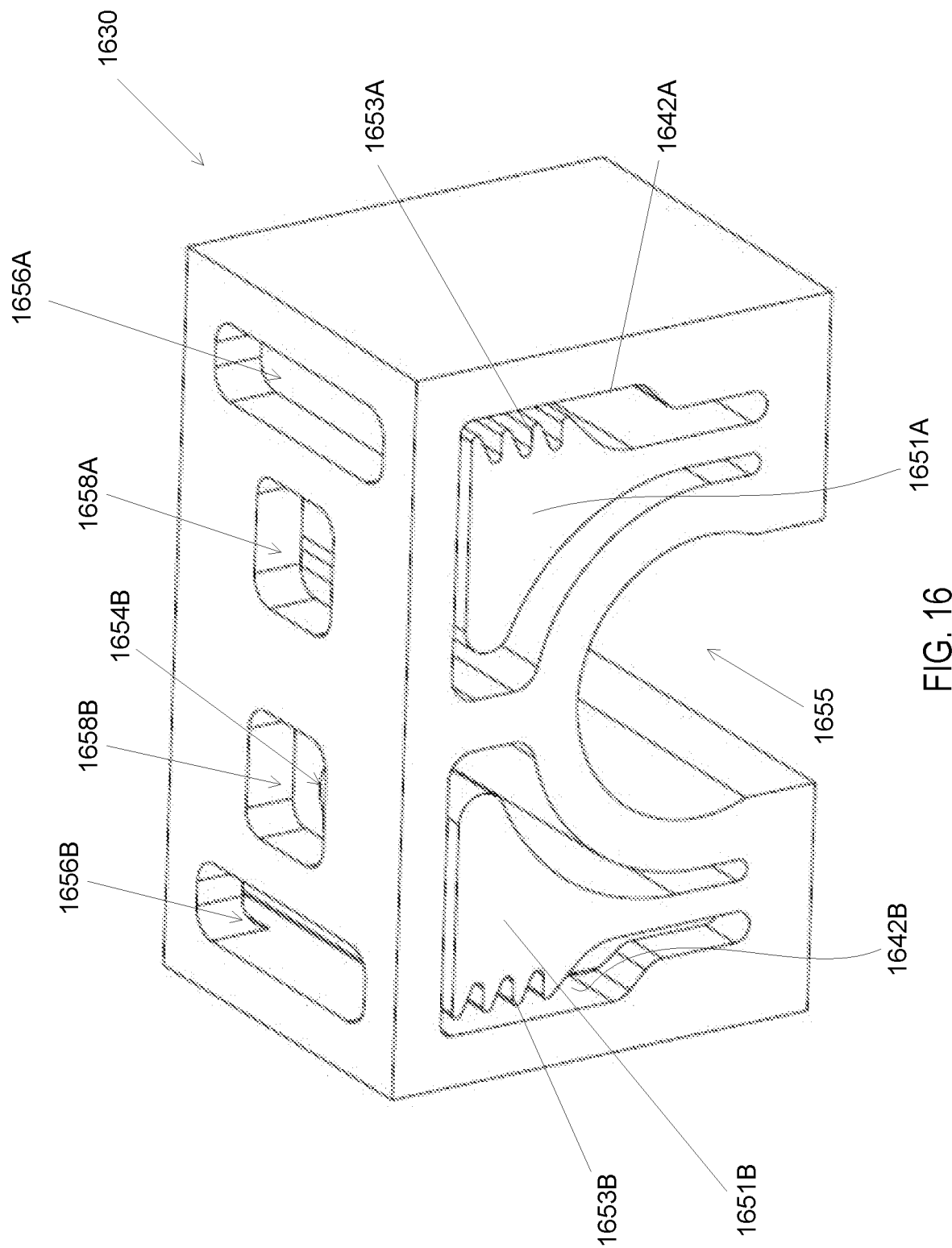
FIG. 16 is a perspective view of a one-piece tether clamping assembly according to some embodiments.
Figure 17:
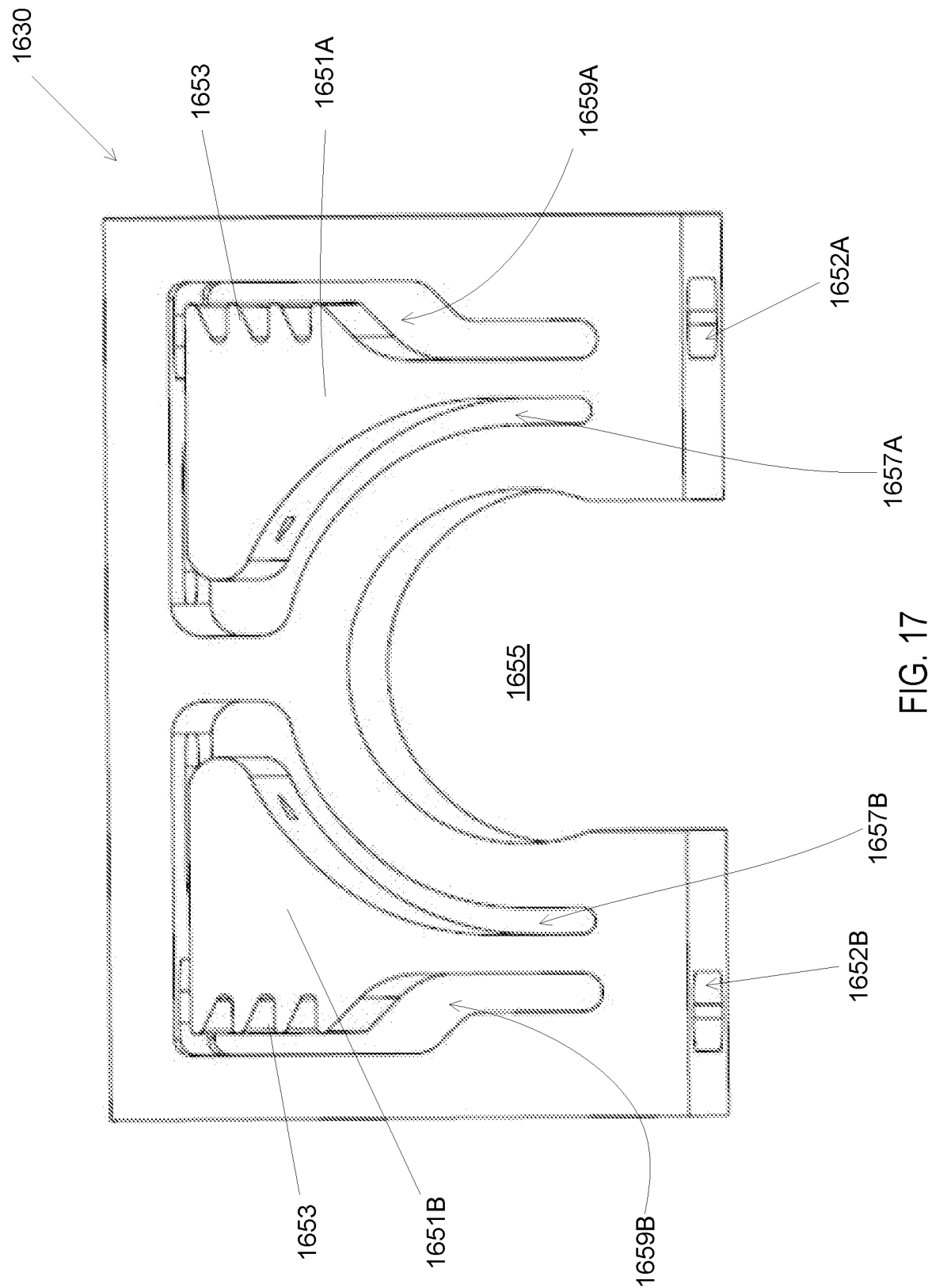
FIG. 17 is a side elevation view of the tether clamping assembly of FIG. 16.
Figure 18:
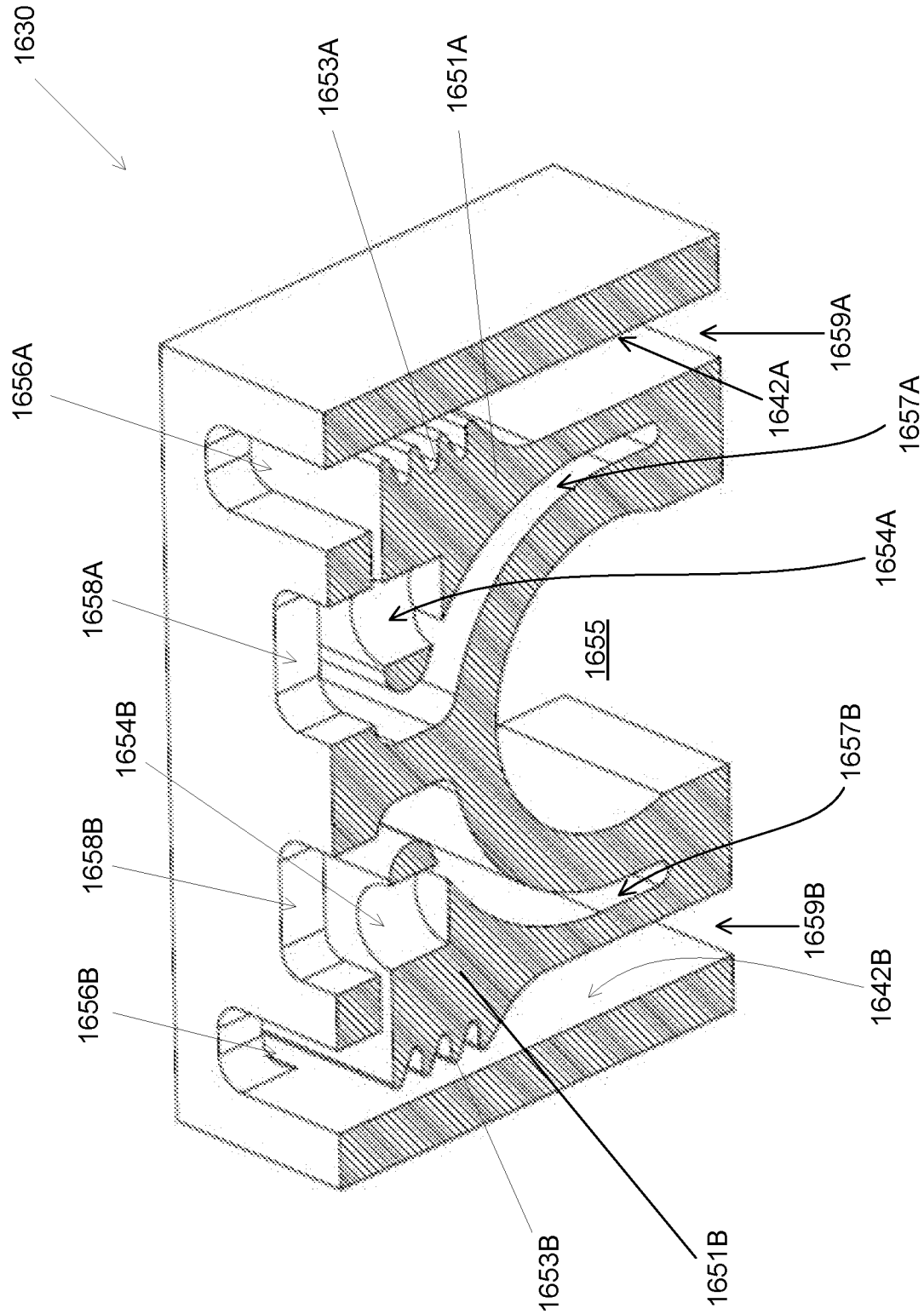
FIG. 18 is a cross-sectional view of the tether clamping assembly of FIGS. 16 and 17.

FIGS. 16-18 depict still another embodiment of a tether clamping assembly 1630 that may be used in connection with a fixation assembly, such as a spinal fixation assembly. Tether clamping assembly 1630 is configured to receive two portions of a tether (not shown) therethrough so as to define a loop and tighten the loop around a spinal feature or other anatomical feature, as previously discussed. However, tether clamping assembly 1630 differs from the other coupling assemblies described herein in that tether clamping assembly 1630 is defined by a unitary structure rather than two separate structures coupled together. More particularly, tether clamping assembly 1630 comprises an internal structure defined by two locking members 1651A and 1651B.

Locking members 1651A and 1651B are movably (in the depicted embodiment, pivotably) positioned in respective internal chambers so as to define empty spaces on either side. More particularly, locking members 1651A and 1651B are positioned in between respective inner spaces 1657A/1657B and outer spaces 1659A/1659B. In the depicted embodiment, opposing tether receiving paths are defined by outer spaces 1659A/1659B, as best seen in the cross-sectional view of FIG. 18.

Respective outer surfaces of locking members 1651A and 1651B may comprise a plurality of projections 1653 or may otherwise be surface roughened relative to the opposing inner surfaces 1642A and 1642B. Thus, both passages of coupling mechanism 1630 are configured to be self-locking with respect to tether portions received therethrough. In order words, upon extending respective tether portions through these passages and applying tension in the upward direction (relative to the orientation in FIGS. 16 and 17), the tether portions retain the applied tension and are prevented, or at least inhibited, from being pulled in the opposite, downward direction. The opposing surfaces defining passages 1659A and 1659B, along with their respective surface features, are therefore another example of means for self-locking a tether within a rod-coupling assembly.

Surface 1642A, together with the surface upon which projections 1653A are formed, define a first passage 1659A for receiving a first portion of a tether, such as a flexible band, therethrough. Similarly, surface 1642B, together with the surface upon which projections 1653B are formed, define a second passage 1659B for receiving a second portion of the tether therethrough. These passages have openings on opposite ends of tether clamping assembly 1630, namely, upper openings 1656A and 1656B and respective lower openings 1652A and 1652B.

Preferably, locking members 1651A and 1651B are pivotably movable within their respective chambers. Thus, outer spaces 1659A/1659B may be configured, respectively, to allow locking members 1651A and 1651B to be resiliently biased towards the center of tether clamping assembly 1630 by a predetermined distance. Correspondingly, the width of the opposing passages defined in part by locking members 1651A and 1651B may be slightly increased as locking members 1651A and 1651B pivot in this manner. In addition, as depicted in the figures, respective base portions of locking members 1651A and 1651B may be narrowed to provide the flexibility to allow for this pivoting/movement.

Because locking members 1651A and 1651B are movable, as previously discussed, preferably the friction differential between the opposing surfaces defining the passages are applied such that the surface on locking members 1651A and 1651B (the movable surfaces) have a greater surface roughness than the opposing non-movable surfaces. Thus, as previously mentioned, the projections 1653 may only be formed on these surfaces of locking members 1651A and 1651B and not on the opposing inner surfaces 1642A and 1642B of the inner chamber of tether clamping assembly 1630.

Tether clamping assembly 1630 further comprises release mechanisms to allow the self-locking feature to be unlocked. In the depicted embodiment, these release mechanisms comprise tether clamping assembly openings 1658A and 1658B which are positioned to allow access to respective locking member openings 1654A and 1654B formed in upper surfaces of locking members 1651A and 1651B. As best shown in the cross-sectional view of FIG. 18, openings 1654A and 1654B may be configured to receive portions of a suitable instrument, such as prongs. In some embodiments, this may allow a user to, for example, squeeze the locking members 1651A and 1651B towards one another and thereby release their respective locks on the tether portions extending through the tether passages extending between upper openings 1656A and 1656B and respective lower openings 1652A and 1652B. Of course, only one of the locking member openings 1654A and 1654B may be engaged, if desired, in order to only unlock the locking/clamping of tether clamping assembly 1630 on one tether portion instead of both portions extending through tether clamping assembly 1630.

Various methods for clamping a tether to a spinal feature or other anatomical feature may also be performed using one or more of the inventive clamping assemblies, or sub-elements of such an assembly, taught herein. For example, in some implementations of such methods, a tether, such as in some such implementations a flexible band, may be extended in a loop around an anatomical feature, such as around a spinal transverse process or spinal lamina, for example. An elongate member, such as a rigid rod, may be coupled with a clamping assembly, such as any of the various clamping assemblies disclosed herein.

A first end of the tether may then be fed through a first passage of the clamping assembly. In some implementations, the first passage may be defined by a first pair of opposing surfaces having distinct surface roughnesses. In some such implementations, a movable surface (relative to the elongate member) may comprise a greater surface roughness that an opposing non-movable surface. Thus, for example, the movable surface may be formed with a plurality of grooves and/or projections to increase the surface roughness and/or grip on the tether.

In some implementations, a second end of the flexible tether opposite from the first end may also be fed through a second passage, which may be defined by a second pair of opposing surfaces also having distinct surface roughnesses. In some implementations, the first end of the flexible tether may be fed through the first passage and/or the second end of the flexible tether may be fed through the second passage to automatically lock the flexible tether in place about the anatomical feature without the use of a secondary locking feature, such as a locking cap, set screw, or the like, to prevent a size of the loop from increasing.

In some implementations, the clamping assembly may comprise an inner coupling piece and an outer coupling piece configured to receive the inner coupling piece. In some such implementations, the first passage and the second passage may be at least partially defined by an inner surface of the outer coupling piece and an outer surface of the inner coupling piece.

In some implementations, the clamping assembly may also be unlocked following the self-locking procedure. For example, a user may unlock one or both tether portions using a means for unlocking a self-locking tether, such as the locking member openings 1654A and 1654B formed in upper surfaces of locking members 1651A and 1651B, for example. This may allow for readjustment or loosening of a tether clamping assembly following self-locking of the tether within the assembly.

Figure 19:
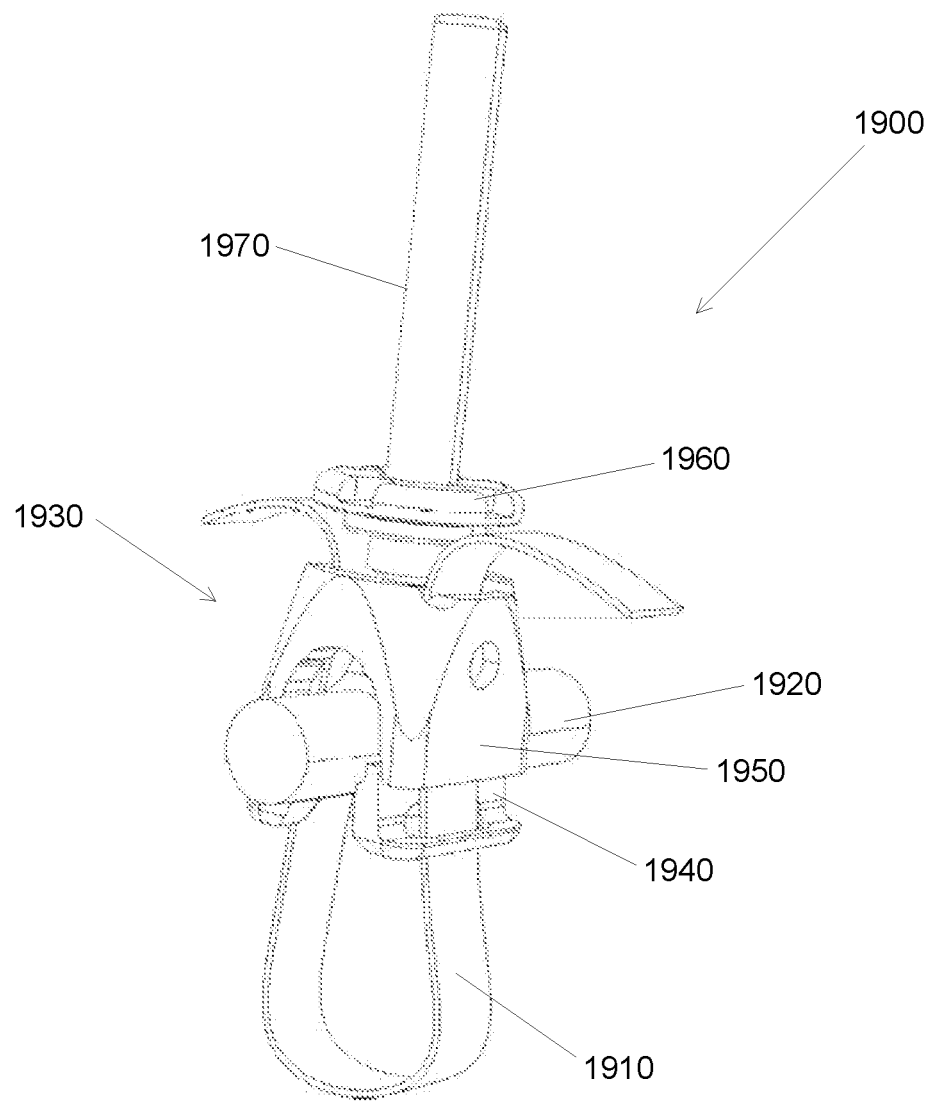
FIG. 19 is a perspective view of a tether clamping assembly according to another embodiment.

FIG. 19 is a perspective view of a spinal fixation assembly 1900 according to still other embodiments. Assembly 1900 comprises a tether 1910 that is configured to engage an anatomical feature, such as a spinal lamina, transverse process, and/or other spinal features in preferred embodiments. Tether 1910 in some embodiments, may comprise a flat, flexible band resembling, for example, a piece of tape. In preferred embodiments, tether 1910 may be flat and/or smooth on both opposing sides. For example, in preferred embodiments, tether 1910 may be devoid of locking teeth and/or other projections.

Assembly 1900 further comprises a tether clamping assembly 1930 configured to engage and couple a coupling member, such as a cylindrical rod 1920 or another elongate member, with the tether 1910 so as to facilitate coupling of a patient's spine in a desired position without use of pedicle screws or other similar bone-invasive components. As further described below, tether clamping assembly 1930 comprises an inner coupling piece 1940 and an outer coupling piece 1950 configured to nestably engage the inner coupling piece 1940, as depicted in FIG. 19. Assembly 1900 further comprises a locking cap 1960 configured to engage tether clamping assembly 1930. More particularly, in this embodiment, locking cap 1960 is configured to threadably engage a threaded shaft extending from inner coupling piece 1940 to pinch and thereby lock tether 1910 in place between cap 1960 and outer coupling piece 1950.

Figure 20:
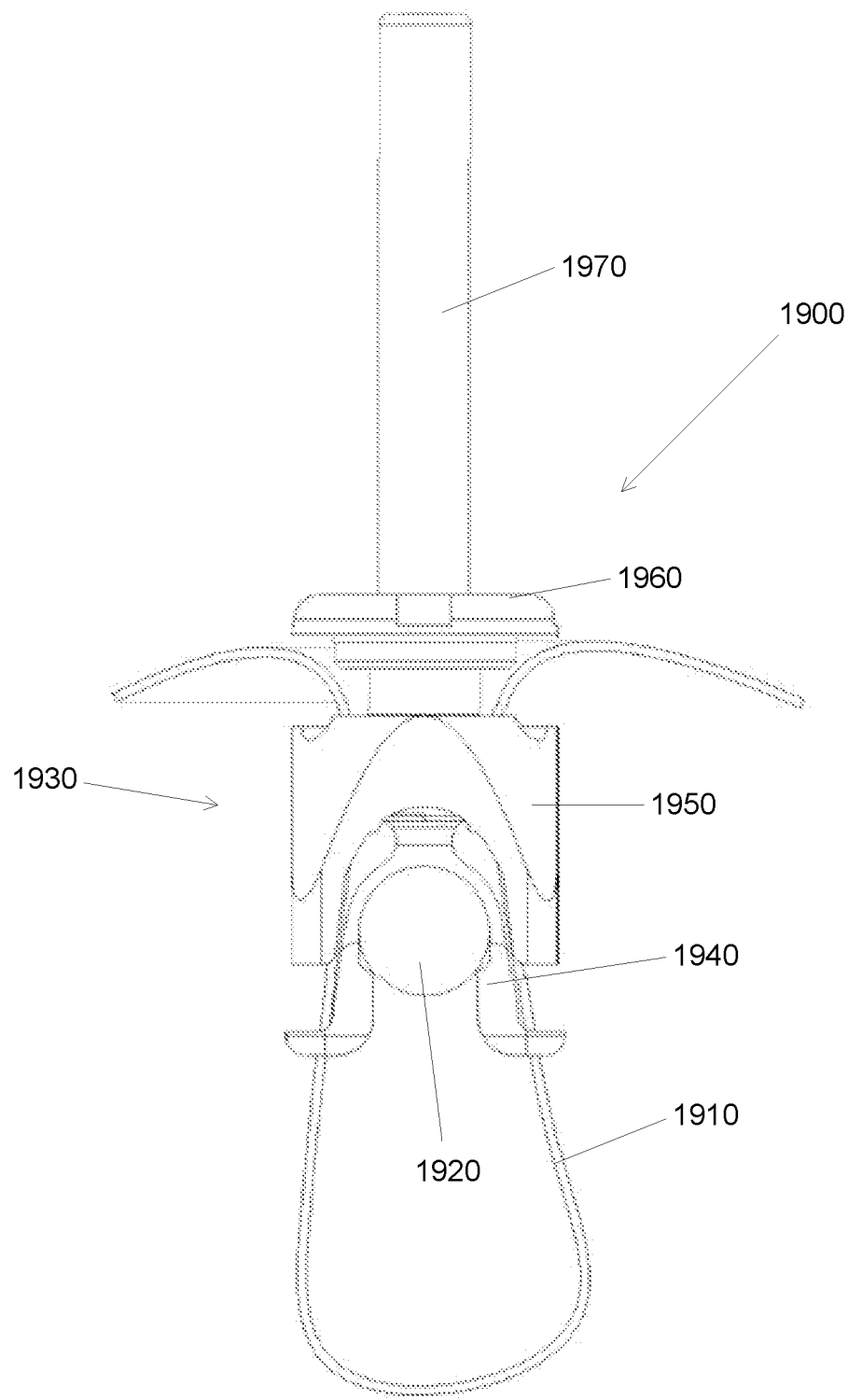
FIG. 20 is a side elevation view of the tether clamping assembly of FIG. 19.
Figure 21:
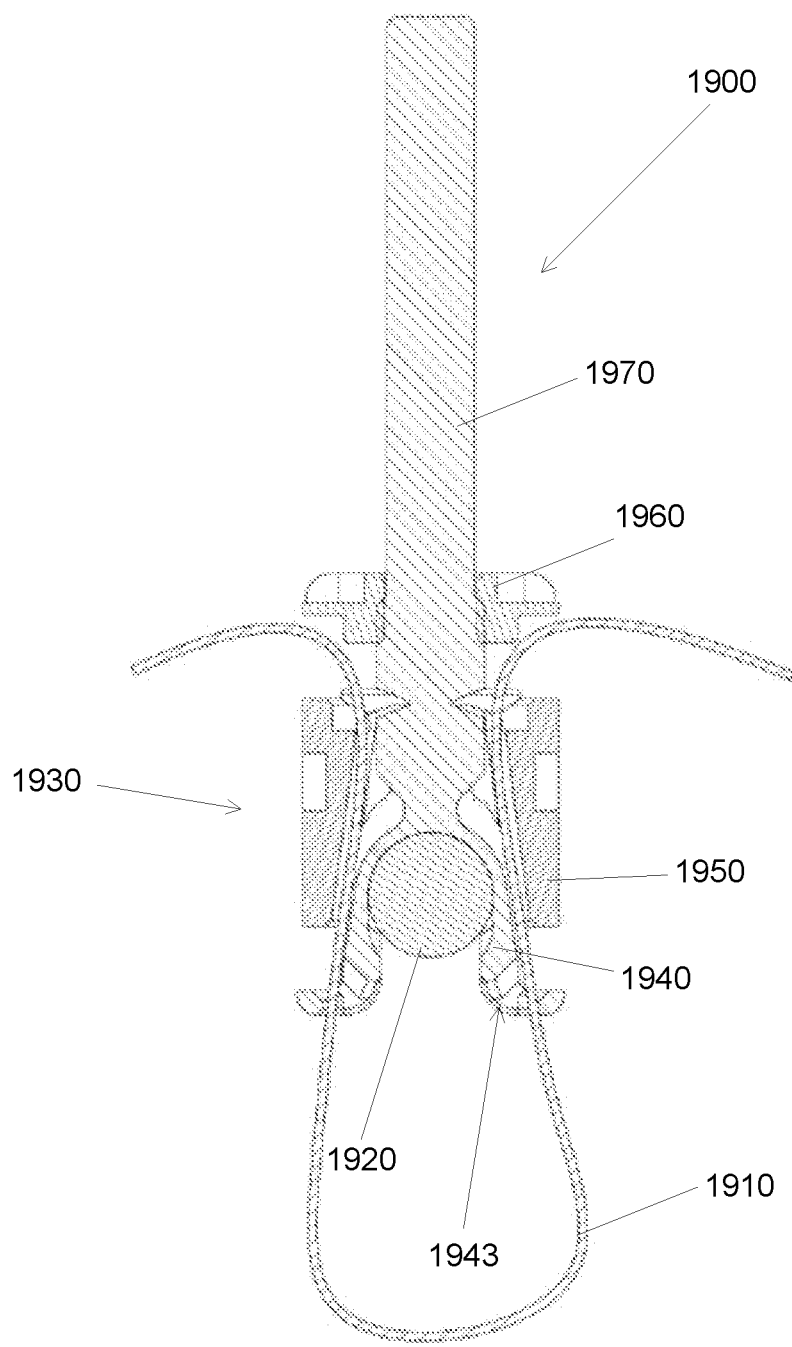
FIG. 21 is a cross-sectional view of the tether clamping assembly of FIG. 20.

FIGS. 20 and 21 illustrate, respectively, a side elevation view and a corresponding cross-sectional view of assembly 1900. As shown in these figures, opposing passages are defined for two portions of tether 1910 to allow for defining a loop and then clamping tether 1910 to lock the loop in place. These opposing passages are defined by various features of the two nestable coupling pieces, namely, inner coupling piece 1940 and outer coupling piece 1950. More particularly, a first passageway for a first portion of tether 1910 is defined by a first inner surface (or, in alternative embodiments, a first portion of an inner surface) of outer coupling piece 1950 and an outer surface (or, in alternative embodiments, a first portion of an outer surface) of inner coupling piece 1940. These passages are further defined by opposing apertures 1943 that are formed in opposing, protruding leg portions of inner coupling piece 1940 at one end and by opposing openings defined between a shaft portion 1970 of inner coupling piece 1940 and outer coupling piece 1950.

In preferred embodiments, clamping assembly 1930 is self-locking. In other words, by advancing tether 1910 through one or both of the aforementioned opposing passages, the tension on tether 1910 alone results in a tightening and/or at least partial locking of tether 1910 in clamping assembly 1930 without use of additional fasteners or fastening steps. Thus, although a locking cap 1960 is provided, in the depicted embodiment and other preferred embodiments, an at least partial locking in which a force differential between pulling the tether loop defined by tether 1910 in a locking direction and an unlocking direction opposite from the locking direction is provided such that tightening can be performed prior to coupling and/or tightening of cap 1960. However, cap 1960 is preferably, and in the depicted embodiment is, configured to further seat and approximate the two coupling pieces and thereby further both lock the tether in place therebetween and lock the rod or another suitable longitudinal and/or coupling member seated in the clamping assembly.

In the depicted and other preferred embodiments, no additional instruments, and/or no other forces (such as manual tension) is required in order to maintain tension on the free ends of the tether to lock the tether in place. In other words, unlike prior art systems for clamping a tether, which often require complicated, bulky, and expensive instruments to maintain tension while locking, simply applying tension to the loop by extending the tether in the locking direction through the one or more passages to tighten the loop will automatically lock the tether in place and maintain the tension. This automatic, self-locking feature, in preferred embodiments and implementations, is therefore expected to result in decreased surgery time, decreased use of various tensioning instrumentation, and likely decreased costs and improved results.

The accompanying figures further illustrate that inner coupling piece 1940 defines a slot 1945 for receipt of a rod 1920 or other elongate and/or rigid coupling member therethrough. Preferably, slot 1945 is shaped to match, or at least substantially match, the shape of the outer surface of rod 1920 such that rod 1920 may be engaged/gripped by slot 1945. In some embodiments, slot 1945 may comprise one or more engagement features, such as teeth, grooves, spikes, or a contoured and/or roughened surface to further facilitate a firm engagement between rod 1920 and inner coupling piece 1940.

In some embodiments, one or both of the coupling pieces may comprise features that allow for resilient receipt of rod 1920 therein, such that rod 1920 may be snapped and locked (at least from a translation standpoint; longitudinal movement may be allowed after locking in some embodiments) in place. Thus, in the depicted embodiment, inner coupling piece 1940 comprises opposing ledges 1941 that may be curved to match the curvature of rod 1920. It may also, or alternatively, be desired to provide a ledge 1941 with an edge that may be the most, or only, point of direct contact with rod 1920 to bite into rod 1920 and lock it in place. This edge can be best seen in FIG. 22.

Figure 22:
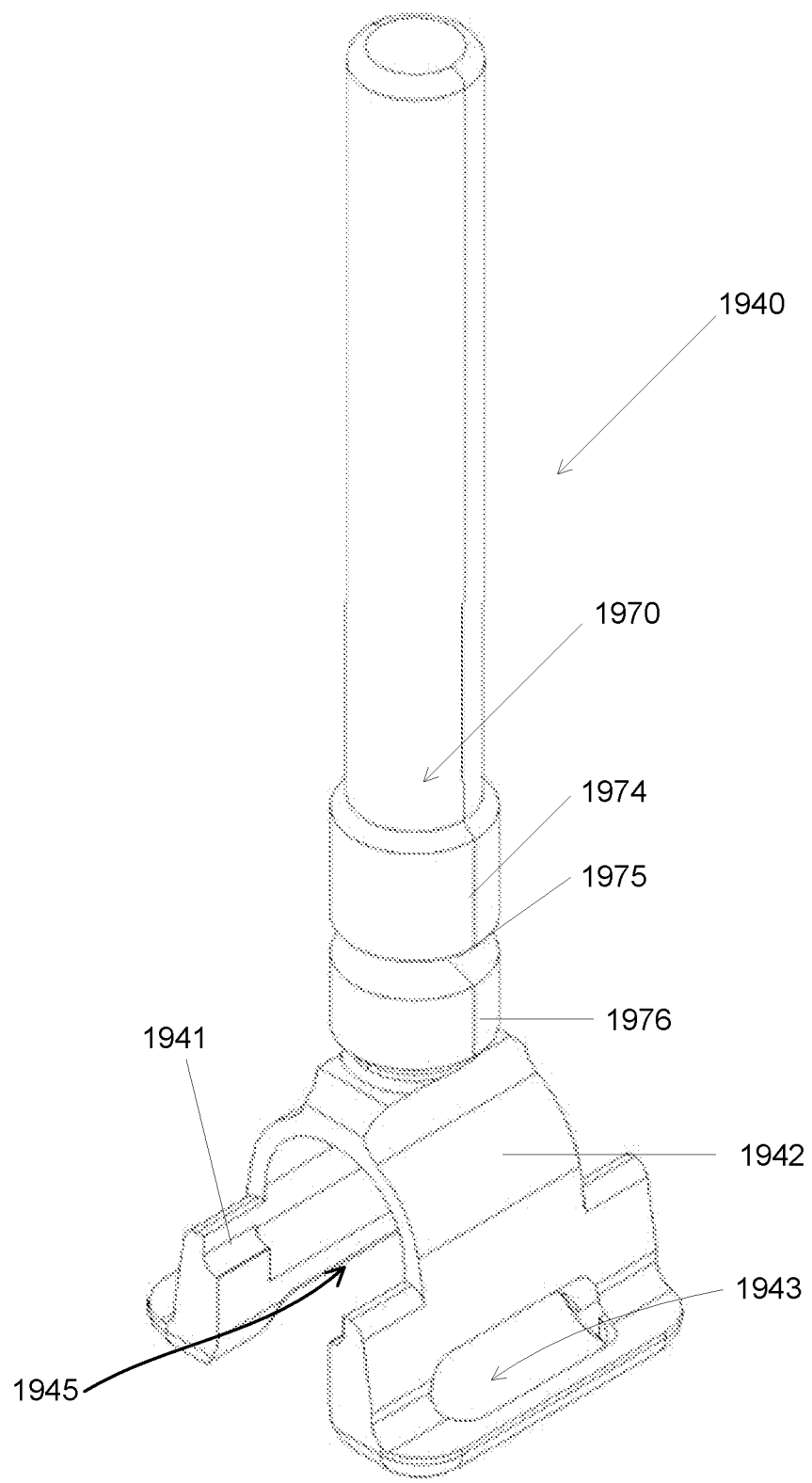
FIG. 22 is a perspective view of an inner coupling piece of a tether clamping assembly according to some embodiments.

In the depicted embodiment, these ledges 1941 comprise partial ledges that are positioned on opposite sides both from the perspective of the dimension of inner coupling piece 1940 corresponding to (parallel to) the elongated axis of rod 1920 and in the direction perpendicular to this direction across the width of rod 1920, as shown in FIG. 22. The presence of such one of more ledges 1941 may facilitate a secure coupling of rod 1920, in some cases by way of a snap-fit engagement. Thus, it may be preferred to allow the opposing arms of inner coupling piece 1940 defining outer surfaces 1942 to be slightly flexible to allow for expanding to receive rod 1920, but preferably resiliently flexible to allow for resuming its previous shape and/or size to grip rod 1920. Of course, alternative embodiments are contemplated in which this ridge extends the entire length of the opposing legs of inner coupling piece 1940 or is omitted.

A desired coupling of rod 1920 may also be provided by providing for a certain amount of flexibility in the opposing legs of inner coupling piece 1940. In the depicted embodiment, this may be provided for, at least in part, by making the central hub portion of inner coupling piece 1940 from which the opposing legs extend have a narrower width than the portions of the legs that define apertures 1943, as also shown in FIG. 22. Apertures 1943 may be provided to guide the tether into the clamping features of the assembly 1930 and to prevent or at least inhibit twisting and/or misalignment of the tether. Thus, in embodiments utilizing a tether have a rectangular shape in cross-section, as show in the accompanying figures, apertures 1943 may define slots having a similar shape and may therefore be referred to herein as "tether guide slots."

In some embodiments providing a snap-on feature, slot 1945 may also be roughened, textured, and or provided with teeth or other engagement features, as mentioned above.

At the upper end (from the perspective of FIG. 22) of inner coupling piece 1940, a shaft 1970 extends from the portion of inner coupling piece 1940 defining the outer surfaces 1942 that partially define the opposing passages for tether 1910. Shaft 1970 comprises a frangible or weakened portion 1975. This may allow for the upper portion, which may facilitate coupling of cap 1960, to be removed during surgery by breaking shaft 1970 at weakened portion 1975. Shaft 1940 further comprises a lower coupling portion 1976, which is preferably threaded, along with an upper coupling portion 1974, a portion of which may also be threaded. Shaft 1940 may therefore serve as a guidepost for coupling of various elements of assembly 1930, including outer coupling piece 1950 and cap 1960. This may allow for cap 1960 to be threaded onto the portion of inner coupling piece 1940 that is to remain within the patient's body following the procedure by providing a starting point above the weakened region 1975.

Of course, rather than providing a weakened region, in alternative embodiments, a guide post may be provided with other features that may be removable to allow for removal of the upper portion/guide post portion of the assembly following coupling of a cap and/or other elements of the assembly. For example, in other embodiments, an end of upper coupling portion 1974 may be threaded and may fit within a female threaded portion of lower coupling portion 1976, or vice versa. As another alternative, in some embodiments a snap-fit coupling or other means for removable coupling may be provided.

Figure 23:
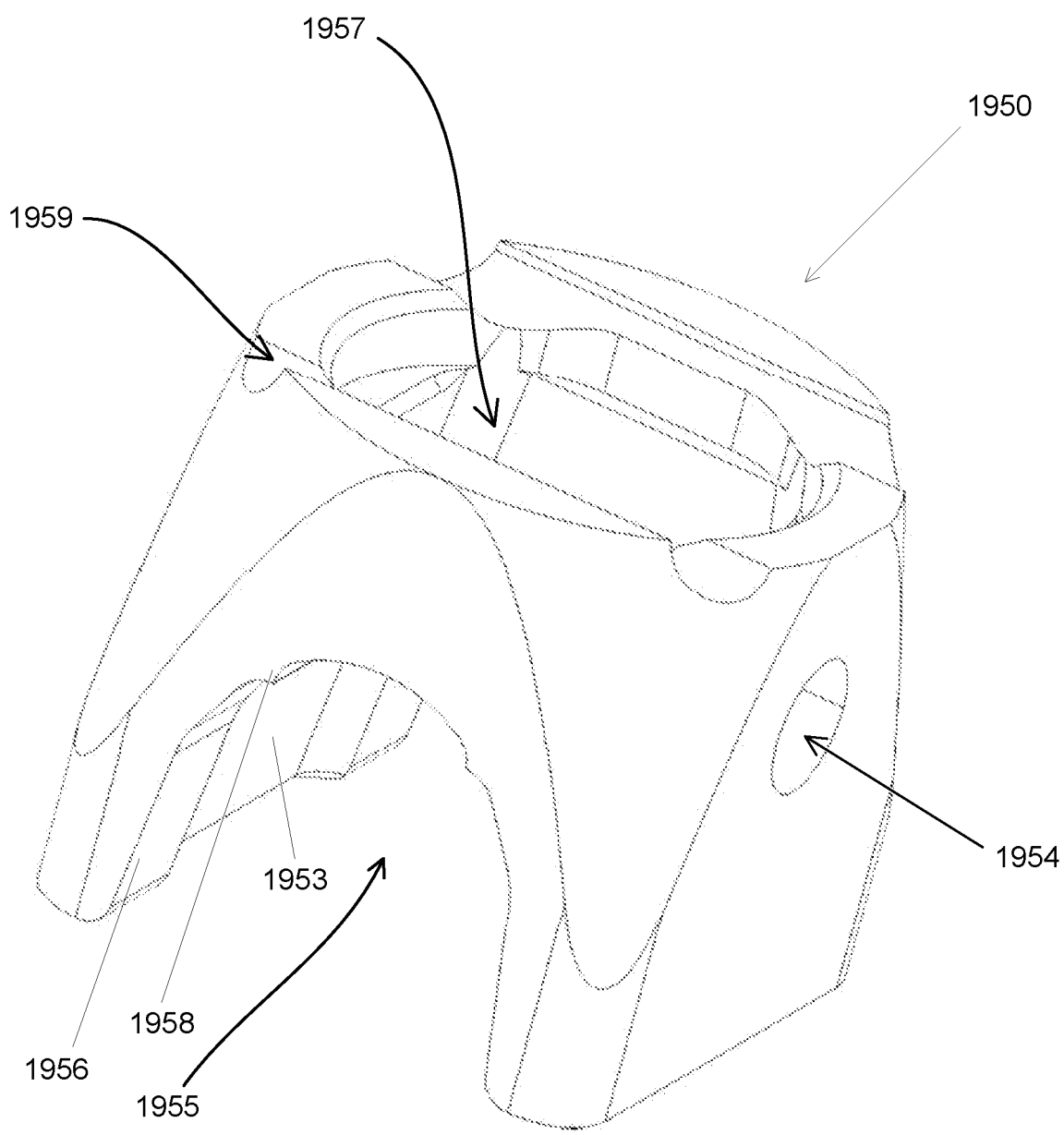
FIG. 23 is a perspective view of an outer coupling piece of a tether clamping assembly according to some embodiments.

FIG. 23 is a perspective view of outer coupling piece 1950 separated from the other elements of assembly 1900. As best seen in this figure, outer coupling piece 1950, like inner coupling piece 1940, comprises a slot 1955 that may be configured to be aligned with slot 1945 upon coupling inner coupling piece 1940 with outer coupling piece 1950. Also, by coupling inner coupling piece 1940 with outer coupling piece 1950, a pair of opposing passages are defined for receipt of separate portions of a flexible tether 1910 therethrough, as previously mentioned.

The upper portion of outer coupling piece 1950 comprises an opening 1957 that is configured to receive shaft 1970 of inner coupling piece 1960 therethrough. Because tether 1910 exits adjacent this opening, the depicted embodiment further comprises opposing pairs of grooves 1959, both of which define paths for receipt of tether 1910. In other words, the width of tether 1910 may at least substantially match the distance between adjacent grooves 1959 on both sides of outer coupling piece 1950 so that the ends (perpendicular to the length) of tether 1910 fit within grooves 1959. Grooves 1959 may also prevent or at least inhibit lateral translation of the tether 1910 as the locking cap 1960, if present, is tightened.

Grooves 1959 may at least substantially the width of the tether 1910, as described above, but the portion of the upper surface of outer coupling piece 1950 in between these grooves 1959 may also be recessed relative to the opposing rims of outer coupling piece that face each other in a direction perpendicular to the direction of tether 1910, as shown in FIG. 23. This may prevent over-compression of tether 1910 when cap 1960 is applied and/or may provide for increased control of the tether clamping that may take place therein.

Outer coupling piece 1950 further comprises a notch 1954, which may be configured to engage a corresponding protruding element of a suitable surgical instrument. Although not visible in FIG. 23, in some embodiments, a similar notch may be formed on the opposite side of outer coupling piece 1950.

Preferably, clamping assembly 1930 is configured such that tether 1910 can be clamped and/or locked in clamping assembly 1930 so as to allow tether 1910 to move through one or both opposing passages in a first direction to lock the tether in place but so as to prevent, or at least substantially prevent and/or provide a force differential, tether 1910 from moving through one or both passages in a second direction opposite from the first direction. Thus, with respect to the view of FIGS. 20 and 21, tether 1910 may be advanced in an upward direction along both opposing passages, thereby resulting in a tether loop that gets smaller to apply a force to a spinal or other anatomical feature, but may be prevented, or at least relatively inhibited from being advanced in a downward direction to enlarge the size of this tether loop. In some embodiments, the greater the force applied in a locking direction, the tighter the lock, and therefore the more difficult it is to move the tether in an opposite direction from the locking direction. Moreover, in some embodiments, this locking/force differential may be applied without use of cap 1960 or any other locking feature/step.

In some embodiments, this self-locking feature may be enhanced by providing a friction differential between the two opposing surfaces through which one or more portions of tether 1910 are received. Preferably, this friction differential is applied such that a movable surface has a greater surface roughness than an opposing non-movable surface. Because, as discussed in greater detail below, in some implementations of inventive methods disclosed herein, the inner coupling piece 1940 may be coupled with a rod 1920 or other elongate member prior to coupling outer coupling piece 1950 with inner coupling piece 1940, outer coupling piece 1950 may be considered the "moveable" element of clamping assembly 1930.

In the depicted embodiment, however, the aforementioned locking/force differential may be provided without providing the friction differential described above. For example, the embodiment depicted in FIGS. 19-23 provides for self-locking of tether 1910 by virtue of a wedge-locking feature. This locking feature is preferably provided, and with respect to the depicted embodiments is provided, by simply applying increased tension to the loop end of the tether 1910 by extending one or both free ends of the tether 1910 through assembly 1930, which may take place by simply pulling the tether against assembly 1930 to shorten the loop around an anatomical feature to increase the tension on the loop end. Simply releasing the free end or ends of the tether 1910 then automatically locks the tether 1910 in place. Similarly, loosening/unlocking may be provided by simply applying increased tension to the free end or ends of the tether 1910 relative to the loop end to temporarily release the lock and allow the tether 1910 to extend through the clamping features of assembly 1930 in the unlocking direction.

Assembly 1900 further comprises a dual-locking feature, namely, it is configured to provide simultaneous locking of tether 1910 and locking/tightening of the grip on rod 1920. This may be provided in part due to the wedging of outer coupling piece 1950 onto inner coupling piece 1940. Thus, as the tension on tether 1910 is increased in the tightening direction by pulling one or both ends of tether 1910 through the two opposing passages defined by outer coupling piece 1950 and inner coupling piece 1940, not only is tether 1910 pinched more tightly therebetween to prevent it from being loosened, but, at the same time, the slot 1945 created by the inner surface of inner coupling piece 1940 is squeezed against the rod 1920 more tightly to further lock the tether clamping assembly 1930 in place with respect to the rod 1920. This feature is provided for by virtue of the wedge lock previously described, in which two tapering surfaces are wedged against each other (with the tether 1910 therebetween) in combination with making the inner coupling piece 1940 flexible so that the size of slot 1945 can vary to facilitate this compression. Preferably, as shown in FIGS. 19 and 20, these tapering surfaces are frusto-conical surfaces.

Assemblies 1900 and 1930 may also be configured to facilitate loosening of the grip/lock/clamp on the tether 1910 for readjustment. As previously mentioned, locking of the tether may be accomplished automatically by engaging the tether 1910 between the opposing surfaces of the inner coupling piece 1940 and the outer coupling piece 1950 and pulling the tether 1910 in the locking direction with an opposite force on assembly 1930 to decrease the size of the tether loop, with the optional cap 1960 to further enhance this locking of the tether 1910 and/or the rod 1920 once a desired force and/or position of the assembly has been achieved. This may allow for sequential tightening of various elements of a spinal fixation system without leaving instrumentation in place while moving to a new location within the system, which may also reduce the instrument tray and decrease surgery time.

In some embodiments, including those depicted in the accompanying figures, the automatic locking, which may take place without tensioning instrumentation due to the features described herein, may take place not only on the tether 1910 but also simultaneously on the rod or other longitudinal member.

If loosening is needed, in preferred embodiments, due to the unique features described herein, the tether may be loosened by simply pulling or otherwise tensioning one or both of the free ends of the tether, which loosens the grip on the tether and allows it to pass through the one or more passages described herein in the unlocking direction.

In the event that the clamp provided by the inner and outer coupling pieces is too tight, such as when a locking cap/nut has been applied, in some embodiments and implementations, the outer coupling piece 1950 may be separated from the inner coupling piece 1940 to allow for loosening using suitable instrumentation.

FIG. 19 further illustrates how approximation of inner coupling piece 1940 and outer coupling piece 1950 results in laterally pinching of the portion of inner coupling piece 1940 within which rod 1920 sits. Thus, as explained elsewhere herein, the approximation of inner coupling piece 1940 and outer coupling piece 1950 results in simultaneous clamping of tether 1910 and rod 1920.

In the depicted embodiment, direct contact and therefore fixation and/or locking of rod 1920 or another longitudinal member is provided by not only inner coupling piece 1940 but also outer coupling piece 1950. Indeed, as further illustrated in FIG. 23, a pair of projections or ridges 1958 may be provided within slot 1955 of outer coupling piece 1950, which may prevent or at least inhibit rotation of rod 1920. In some embodiments, ridges 1958 or another similar feature may only be configured to provide a torsional locking at the time that the tether 1910 is locked in placed. Thus, the torsional locking force may be proportional to the locking force on the tether 1910 and may be increased automatically by increasing the locking force on tether 1910, by way of simply pulling the tether in the locking direction, as described above, and/or by way of applying a final locking element, such as locking cap 1960.

By providing for lateral contact/force with rod 1920 via ridges 1941 of inner coupling piece 1940 and upper contact/force with rod 1920 by way of projections 1958 on outer coupling piece 1950, the approximation of inner coupling piece 1940 and outer coupling piece 1950 may provide for locking that, like the locking on the tether 1910, increases automatically as the tension on the loop end is increased.

As also illustrated in FIG. 23, a groove 1953 may be provided along one or more opposing inner surfaces of outer coupling piece 1950 to provide a path/seat for a tether. The protruding surfaces 1956 sitting above these grooves provide a surface for direct contact with an outer surface of inner coupling piece 1940, as best illustrated in FIG. 19. This allows the outer coupling piece 1950 to compress the inner coupling piece 1940 as the two coupling pieces are wedged and nested together. These surfaces may be part of and/or continuous with the surfaces defining the passages previously mentioned, as shown in the drawings. In alternative embodiments, however, they may be entirely distinct surfaces.

By providing a feature, such as ledge 1941, that serves as a lower stop to the rod 1920, the rod 1920 may be prevented from being pushed out the bottom of slot 1945 as outer coupling piece 1950 is squeezed against inner coupling piece 1940.

Figure 24:
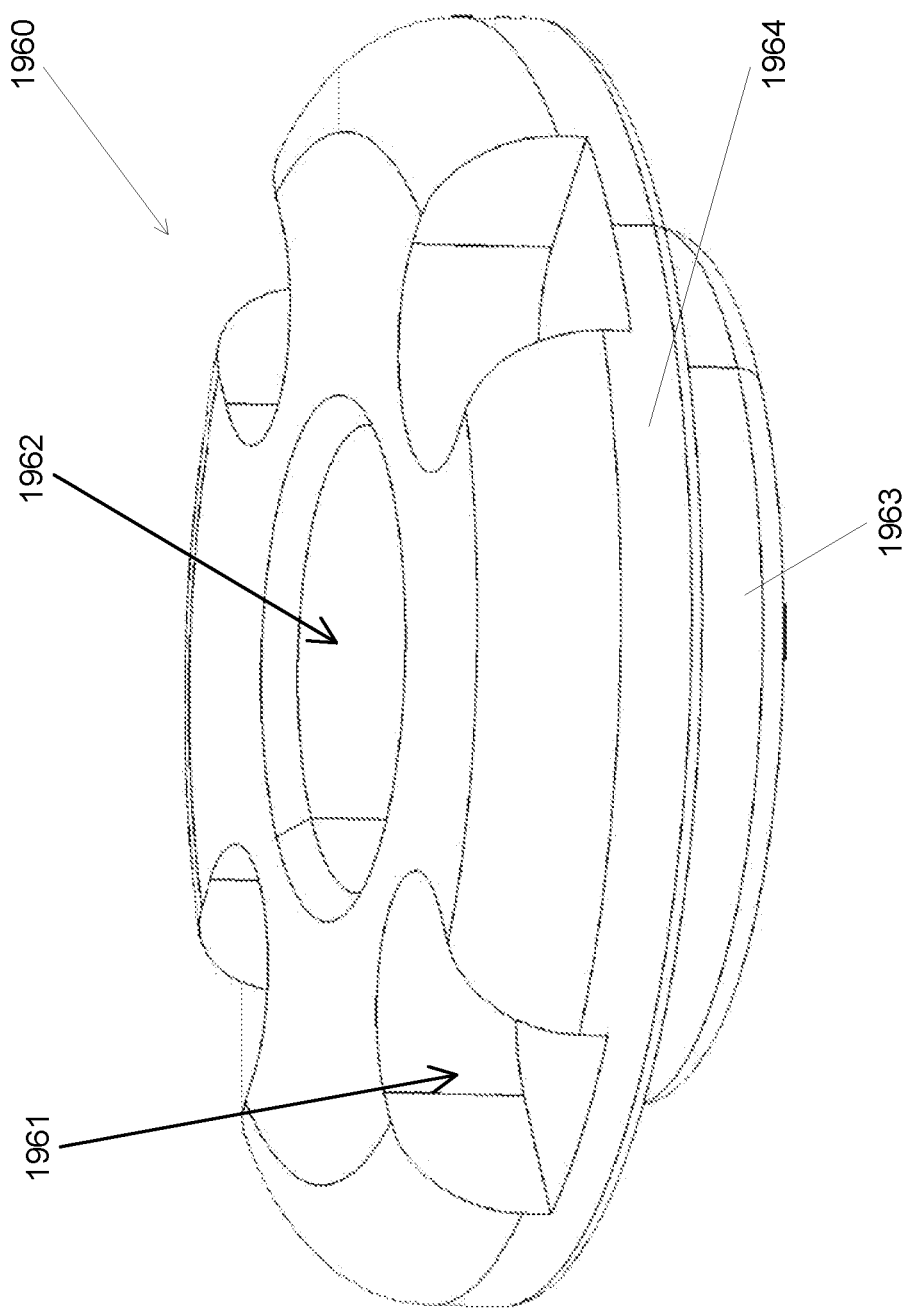
FIG. 24 is a perspective view of a threaded cap that may be used in connection with one or more of the tether clamping assemblies disclosed herein.

FIG. 24 is a perspective view of cap 1960 of spinal fixation assembly 1900 according to some embodiments. Cap 1960 comprises a flanged portion 1964, which is configured to pinch a portion of tether 1910 against an upper surface of outer coupling piece 1950. Cap 1960 further comprises a female threaded opening 1962 configured to engage the threads of shaft 1970 of inner coupling piece 1940. The upper surface of cap 1960 comprises a keyed feature defined by a plurality of circumferentially-spaced grooves that may be configured to receive corresponding prongs of a driver or other similar instrument.

A rim 1963 extends from the lower surface of cap 1960. Rim 1963 may be configured to seat within the periphery of the upper opening provided in outer coupling piece 1950, as best illustrated in FIG. 21. Rim 1963 may also allow for extending the threads provided on cap 1960 to prevent or at least inhibit the threads from stripping. The step provided by rim 1963 may also allow tether 1910 to extend through a corner defined by rim 1963 and outer coupling piece 1950 to increase the gripping force provided therein without excessive pinching, which may otherwise result in cutting and/or fraying of the tether fibers.

As previously mentioned, a portion or, in some such embodiments including the embodiment of assembly 1900, two opposing portions of tether 1910 may be clamped in between flanged portion 1964 of cap 1960 and another portion of assembly 1930, such as the opposing ledges extending in between grooves 1959 on opposing sides of outer coupling piece 1950. Thus, cap 1960 is another example of secondary means for locking a tether within a rod-coupling assembly. Cap 1960 may also serve the function of establishing and/or increasing the lock on the rod and/or tether and/or decreasing the possibility of unwanted loosening/disassembly.

More particularly, because cap 1960 pulls inner coupling piece 1940 and outer coupling piece 1950 together, cap 1960 may increase the clamping force on tether 1910 and, in some embodiments including the depicted embodiment, may simultaneously increase the clamping force on the rod and/or another longitudinal member.

The foregoing specification has been described with reference to various embodiments and implementations. However, one of ordinary skill in the art will appreciate that various modifications and changes can be made without departing from the scope of the present disclosure. For example, various operational steps, as well as components for carrying out operational steps, may be implemented in various ways depending upon the particular application or in consideration of any number of cost functions associated with the operation of the system. Accordingly, any one or more of the steps may be deleted, modified, or combined with other steps.

Further, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced, are not to be construed as a critical, a required, or an essential feature or element.

Those having skill in the art will appreciate that many changes may be made to the details of the above-described embodiments without departing from the underlying principles of the invention. The scope of the present inventions should, therefore, be determined only by the following claims.

The invention claimed is:

1. A method for fixation of a tether to an anatomical feature of a spinal column, the method comprising the steps of:
    extending a flexible tether in a loop around an anatomical feature of a spinal column of a patient;
    coupling an elongate member with an inner coupling piece of a clamping assembly;
    nesting the inner coupling piece within an outer coupling piece of the clamping assembly;
    positioning a first end of the flexible tether through a first passage of the clamping assembly, wherein the first passage is at least partially defined by an outer surface of the inner coupling piece and an inner surface of the outer coupling piece; and
    positioning a second end of the flexible tether opposite from the first end through a second passage, wherein the second passage is at least partially defined by an outer surface of the inner coupling piece and an inner surface of the outer coupling piece; and
    tightening the loop about the anatomical feature with the flexible tether clamped between the inner coupling piece and the outer coupling piece, wherein the clamping assembly is configured such that the step of tightening the loop requires less force than loosening the loop, wherein the step of tightening the loop about the anatomical feature with the flexible tether clamped between the inner coupling piece and the outer coupling piece comprises pulling on one or both loose ends of the flexible tether without use of a secondary locking feature.

2. The method of claim 1, wherein at least a portion of the surfaces defining the first passage are distinct from at least a portion of the surfaces defining the second passage.

3. The method of claim 2, wherein the surfaces defining the first passage are wholly distinct from the surfaces defining the second passage.

4. The method of claim 1, further comprising, after the step of tightening the loop about the anatomical feature with the flexible tether clamped between the inner coupling piece and the outer coupling piece, threadably coupling a locking cap with the inner coupling piece to pinch the flexible tether in between the locking cap and the outer coupling piece.

5. The method of claim 4, wherein the step of threadably coupling the locking cap comprises threadably coupling the locking cap to a partially threaded shaft of the inner coupling piece.

6. The method of claim 5, further comprising breaking the partially threaded shaft of the inner coupling piece at a weakened portion.

7. A method for fixation of a tether to an anatomical feature of a spinal column, the method comprising the steps of:
   extending a tether in a loop around an anatomical feature of a spinal column of a patient;
   coupling a spinal fixation rod with an inner coupling piece of a clamping assembly, wherein the inner coupling piece comprises:
      a slot configured to receive the spinal fixation rod therein; and
      a pair of opposing outer surfaces;
   non-threadably nesting the inner coupling piece within an outer coupling piece of the clamping assembly to apply a temporary lock to the tether in between nested surfaces of the inner coupling piece and the outer coupling piece without the use of any secondary locking features;
   positioning a first end of the tether through a passage of the clamping assembly, wherein the passage is at least partially defined by an outer surface of the inner coupling piece and an inner surface of the outer coupling piece; and
   tightening the loop about the anatomical feature with the tether clamped between the inner coupling piece and the outer coupling piece.

8. The method of claim 7, wherein the step of coupling the spinal fixation rod with the inner coupling piece of the clamping assembly comprises resiliently flexing the slot to receive the spinal fixation rod.

9. The method of claim 8, wherein the slot is at least partially defined by opposing ledges configured to facilitate a snap-fit coupling of the spinal fixation rod within the slot.

10. The method of claim 7, further comprising positioning a second end of the tether opposite from the first end through a passage at least partially defined by an outer surface of the inner coupling piece and an inner surface of the outer coupling piece.

11. The method of claim 10, wherein the passage through which the second end of the tether is positioned is distinct from the passage through which the first end of the tether is positioned to define the loop.

12. The method of claim 7, wherein the temporary lock comprises a temporary wedge lock in between nested surfaces of the inner coupling piece and the outer coupling piece without the use of any secondary locking features.

13. The method of claim 12, wherein the step of applying a temporary wedge lock to the tether in between nested surfaces of the inner coupling piece and the outer coupling piece results in simultaneous tightening of the spinal fixation rod within the slot.

14. A method for fixation of a tether to an anatomical feature of a patient, the method comprising the steps of:
   extending a tether in a loop around an anatomical feature of a patient;
   coupling an elongate member with a clamping assembly, the clamping assembly comprising:
      an inner coupling piece;
      an outer coupling piece; and
      a slot configured to engage the elongate member;
   nesting the inner coupling piece within the outer coupling piece of the clamping assembly;
   positioning the tether at least partially through a passage of the clamping assembly, wherein the passage is at least partially defined between respective portions of the inner and outer coupling pieces;
   tightening the loop about the anatomical feature with the tether clamped between the inner coupling piece and the outer coupling piece; and
   engaging a locking cap with the clamping assembly to lock the tether in place about the anatomical feature, wherein the step of engaging the locking cap with the clamping assembly comprises threadably engaging the locking cap with a shaft portion of the inner coupling piece.

15. The method of claim 14, wherein the slot comprises an integral portion of the inner coupling piece.

16. The method of claim 14, wherein the passage is at least partially defined by an outer surface of the inner coupling piece and an inner surface of the outer coupling piece.

17. The method of claim 14, wherein the clamping assembly is configured such that the step of tightening the loop requires less force than loosening the loop.

18. The method of claim 14, wherein the anatomical feature comprises an anatomical feature of a spinal column.

19. The method of claim 14, wherein the shaft portion of the inner coupling piece comprises a threaded portion and a non-threaded portion.

20. The method of claim 19, wherein the shaft portion comprises a frangible portion, and further comprising a step of, following the step of engaging the locking cap with the clamping assembly, breaking the shaft portion at the frangible portion.

* * * * *